US008608638B2

(12) United States Patent
McGuire

(10) Patent No.: US 8,608,638 B2
(45) Date of Patent: Dec. 17, 2013

(54) METHODS AND SYSTEMS FOR TREATING TINNITUS

(75) Inventor: John F. McGuire, Oceanside, CA (US)

(73) Assignee: The Regents of the University of California, Oakland, CA (US)

( * ) Notice: Subject to any disclaimer, the term of this patent is extended or adjusted under 35 U.S.C. 154(b) by 839 days.

(21) Appl. No.: 12/564,718

(22) Filed: Sep. 22, 2009

(65) Prior Publication Data

US 2011/0071340 A1 Mar. 24, 2011

(51) Int. Cl.
*A61M 21/00* (2006.01)

(52) U.S. Cl.
USPC .............................................. 600/28; 600/25

(58) Field of Classification Search
USPC .................................................... 600/25, 28
See application file for complete search history.

(56) References Cited

U.S. PATENT DOCUMENTS

| | | | | |
|---|---|---|---|---|
| 5,403,262 | A | 4/1995 | Gooch | |
| 6,155,971 | A | 12/2000 | Calhoun et al. | |
| 6,682,472 | B1 | 1/2004 | Davis | |
| 6,846,284 | B2 | 1/2005 | Choy | |
| 6,974,410 | B2 * | 12/2005 | Micheyl et al. | 600/25 |
| 2007/0133832 | A1 | 6/2007 | DiGiovanni et al. | |
| 2009/0018466 | A1 * | 1/2009 | Materna et al. | 600/559 |
| 2009/0099476 | A1 * | 4/2009 | Fogel et al. | 600/559 |
| 2009/0124850 | A1 * | 5/2009 | Moore et al. | 600/28 |
| 2010/0016755 | A1 * | 1/2010 | Henry et al. | 600/559 |
| 2011/0054241 | A1 * | 3/2011 | Jensen | 600/28 |
| 2011/0137111 | A1 * | 6/2011 | Hanley et al. | 600/28 |

FOREIGN PATENT DOCUMENTS

| | | | | |
|---|---|---|---|---|
| WO | WO 01/70110 | A1 * | 9/2001 |
| WO | WO 2007/121446 | A2 | 10/2007 |
| WO | WO 2008/011396 | A2 | 1/2008 |

OTHER PUBLICATIONS

Al-Jassim, "The use of the Walkman mini-stereo system in the management of tinnitus", The Journal of Laryngology and Otology, Jul. 1987, pp. 663-665,vol. 101.
Al-Jassim, "The use of Walkman mini-stereo system as a tinnitus masker", The Journal of Laryngology and Otology, Jan. 1988, pp. 27-28, vol. 102.
Andersson, et al., "Randomized Controlled Trial of Internet-Based Cognitive Behavior Therapy for Distress Associated with Tinnitus", Psychosomatic Medicine, 2002, pp. 810-816, vol. 64, No. 5, American Psychosomatic Society.
Hazell, et al., "Tinnitus I: Auditory mechanisms: a model for tinnitus and hearing impairment", The Journal of Otolaryngology, Feb. 1990, pp. 1-5, vol. 19, No. 1, ORL Medical Publications Limited.
Henry, et al., "Comparison of two computer-automated procedures for tinnitus pitch matching", Journal of Rehabilitation Research and Development, Sep./Oct. 2001, pp. 557-566, vol. 38, No. 5.

(Continued)

*Primary Examiner* — Christine Matthews
*Assistant Examiner* — Sunita Reddy
(74) *Attorney, Agent, or Firm* — Knobbe Martens Olson & Bear LLP

(57) ABSTRACT

Methods and systems for treating tinnitus are provided. Some embodiments include a method of providing a primary audio signal having a primary peak portion substantially centered at about a tinnitus frequency of a patient. The method may also include combining the primary audio signal with a general audio signal to generate a combined sound. The method may also include exposing the patient to the combined sound so that the patient hears the combined sound, to diminish a perception by the patient of tinnitus.

21 Claims, 23 Drawing Sheets

300

(56) References Cited

OTHER PUBLICATIONS

Henry, et al., "New instrumentation for automated tinnitus psychoacoustic assessment", Acta Oto-Laryngologica, 2006, pp. 34-38, vol. 126, Taylor & Francis.
Henry, et al., "Reliability of Tinnitus Loudness Matches under Procedural Variation", Journal of the American Academy of Audiology, Oct. 1999, pp. 502-520, vol. 10, No. 9, Burlington, Ontario.
Jastreboff, et al. "Neurophysiological model of tinnitus: Dependence of the minimal masking level on treatment outcome", Hearing Research, 1994, pp. 216-232, vol. 80, Elsevier Science B.V.
Kaldo-Sandström, et al., "Internet-Based Cognitive-Behavioral Self-Help Treatment of Tinnitus: Clinical Effectiveness and Predictors of Outcome", American Journal of Audiology, Dec. 2004, pp. 185-192, vol. 13, No. 2, American Speech-Language-Hearing Association.
Nodar, "Tinnitus Aurium: An Approach to Classification", Otolaryngology, Jan.-Feb. 1978, pp. ORL-40 through ORL-46, vol. 86, No. 1, Rochester, Minneasota.
Stephens, et al., "Tinnitus: a management model", Clinical Otolaryngology and Allied Sciences, Jan. 14, 1986, pp. 227-238, vol. 11, Blackwell Scientific Publications, Oxford, London, England.
Vernon, et al., "Tinnitus masking: unresolved problems", Ciba Foundation Symposium, 1981, pp. 239-262, vol. 85, Wiley, Amsterdam.

* cited by examiner

500

1104

| | | | |
|---|---|---|---|
| 49 | a′ | A4 (A440) | 440.000 |
| 48 | g#′/a♭′ | G#4/A♭4 | 415.305 |
| 47 | g′ | G4 | 391.995 |
| 46 | f#′/g♭′ | F#4/G♭4 | 369.994 |
| 45 | f′ | F4 | 349.228 |
| 44 | e′ | E4 | 329.628 |
| 43 | d#′/e♭′ | D#4/E♭4 | 311.127 |
| 42 | d′ | D4 | 293.665 |
| 41 | c#′/d♭′ | C#4/D♭4 | 277.183 |
| 40 | c′ **(1-line 8ve)** | C4 (Middle C) | 261.626 |
| 39 | b | B3 | 246.942 |
| 38 | a#/b♭ | A#3/B♭3 | 233.082 |
| 37 | a | A3 | 220.000 |

Figure 12:
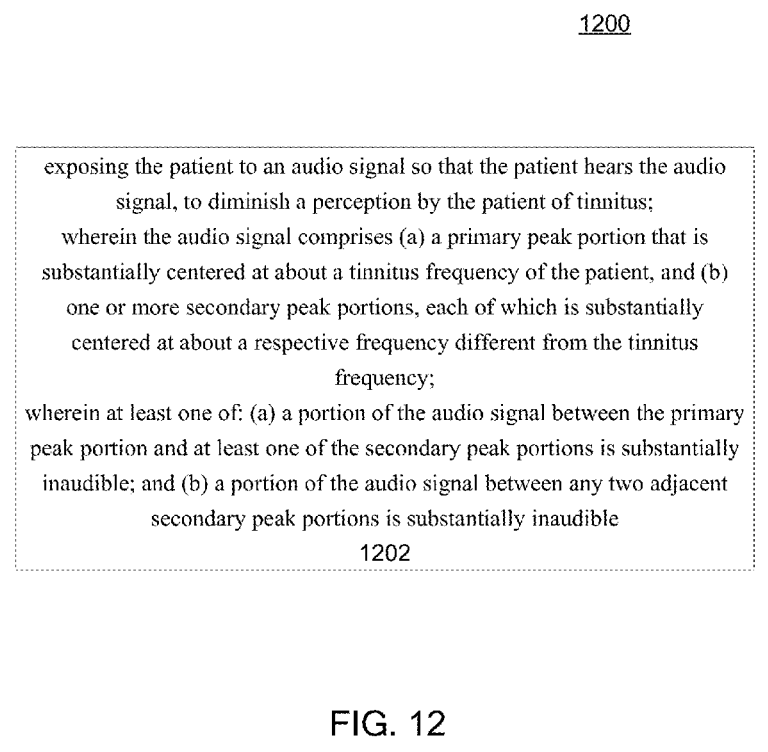

1200 exposing the patient to an audio signal so that the patient hears the audio signal, to diminish a perception by the patient of tinnitus;
wherein the audio signal comprises (a) a primary peak portion that is substantially centered at about a tinnitus frequency of the patient, and (b) one or more secondary peak portions, each of which is substantially centered at about a respective frequency different from the tinnitus frequency;
wherein at least one of: (a) a portion of the audio signal between the primary peak portion and at least one of the secondary peak portions is substantially inaudible; and (b) a portion of the audio signal between any two adjacent secondary peak portions is substantially inaudible
1202

--- determining a tinnitus tonal key based on a tinnitus frequency of a patient
1402

--- providing a plurality of audio signals, each of the audio signals having a different primary tonal key from each other
1404

--- selecting one of the audio signals such that the primary tonal key of the selected audio signal approximately matches the tinnitus tonal key
1406

--- exposing the patient to the selected audio signal so that the patient hears the selected audio signal, to diminish a perception by the patient of tinnitus
1408

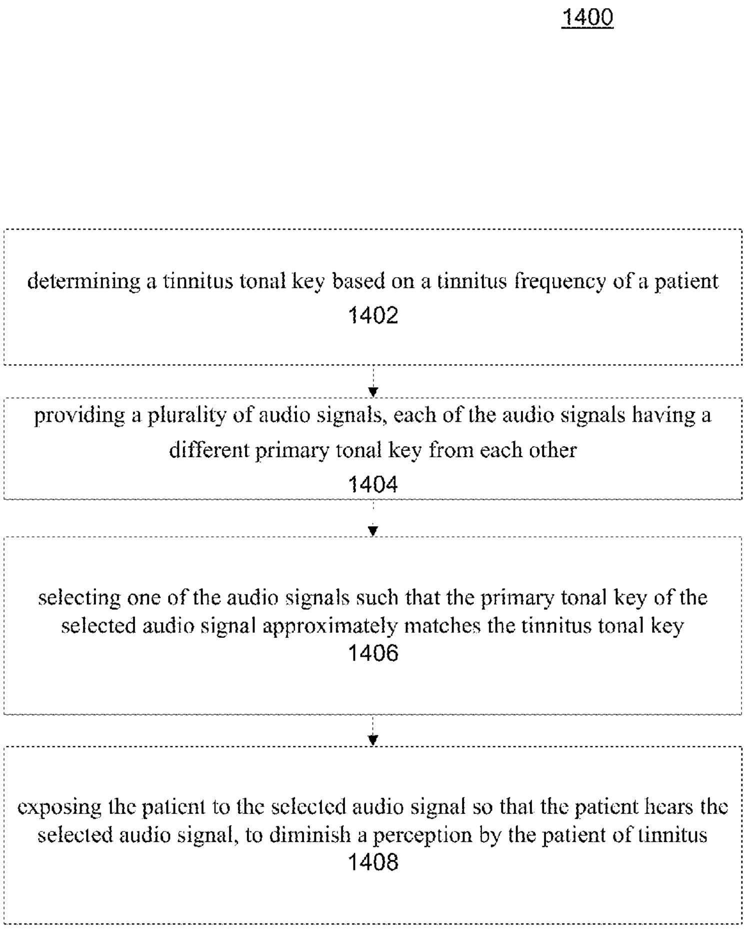

FIG. 14

METHODS AND SYSTEMS FOR TREATING TINNITUS

FIELD

The present invention generally relates to tinnitus and, in particular, relates to methods and systems for treating tinnitus.

BACKGROUND

Tinnitus describes a perceived sound, e.g., ringing, buzzing, whistling, or roaring, that is experienced by a tinnitus sufferer and that does not exist as a physical sound. The condition can be annoying or very painful, and the discomfort caused by tinnitus frequently interferes with a sufferer's sleep. Tinnitus may occur at a specific frequency or over a small frequency range and is frequently constant; however, the specific frequency or small frequency range varies from patient to patient.

SUMMARY

According to various aspects of the subject disclosure, methods and systems for treating tinnitus are provided. Some aspects include a method for treating tinnitus. The method may comprise exposing the patient to an audio signal so that the patient hears the audio signal, to diminish a perception by the patient of tinnitus. The audio signal may comprise (a) a primary peak portion that is substantially centered at about a tinnitus frequency of the patient, and (b) one or more secondary peak portions, each of which is substantially centered at about a respective frequency different from the tinnitus frequency. In some aspects, at least one of: (a) a portion of the audio signal between the primary peak portion and at least one of the secondary peak portions is substantially inaudible; and (b) a portion of the audio signal between any two adjacent secondary peak portions is substantially inaudible.

In some aspects, each of at least one of the one or more secondary peak portions is substantially centered at about a respective octave or sub-octave frequency of the tinnitus frequency. In some aspects, each of at least one of the one or more secondary peak portions is substantially centered at about a respective harmonic or subharmonic frequency of the tinnitus frequency. The method may further comprise determining the tinnitus frequency of the patient. The determining may comprise providing to the patient a range of frequencies of one or more test audio signals. The determining may also comprise, in each of a plurality of trials, receiving from the patient a selection of a frequency, chosen from the range of frequencies, approximately matching the tone of the tinnitus frequency of the patient. The determining may also comprise determining an average tinnitus frequency, based on an average of the selected frequencies from the plurality of trials.

In some aspects, the method may further comprise repeating the tinnitus frequency to determine a recalibrated tinnitus frequency. The audio signal may further comprise a second primary peak portion that is substantially centered at about the recalibrated tinnitus frequency of the patient. The method may further comprise exposing the patient to a second audio signal so that the patient hears the second audio signal, to diminish a perception by the patient of tinnitus. The second audio signal may comprise (a) a second primary peak portion that is substantially centered at about the recalibrated tinnitus frequency of the patient, and (b) one or more tertiary peak portions, each of which is substantially centered at about a respective frequency different from the recalibrated tinnitus frequency. In some aspects, at least one of: (a) a portion of the second audio signal between the second primary peak portion and at least one of the tertiary peak portions is substantially inaudible; and (b) a portion of the second audio signal between any two adjacent tertiary peak portions is substantially inaudible. The method may further comprise combining the audio signal with the second audio signal to generate a combined sound for treating tinnitus.

In some aspects, the method may further comprise adjusting, based on input from the patient, a bandwidth of at least one of (a) the primary peak portion, and (b) the one or more secondary peak portions. In some aspects, a bandwidth of at least one of the primary peak portion and at least one of the one or more secondary peak portions is up to a half octave. The audio signal may further comprise at least one of: a component of white noise, a music signal, a pure tone, a chord, a modulated sound, an ambient sound, and a voice signal. The method may further comprise adjusting, based on input from the patient, an intensity of the primary peak portion in relation to at least one of the one or more secondary peak portions. In some aspects, the method may further comprise adjusting, based on input from the patient, an intensity of at least one of (a) the primary peak portion, and (b) one of the one or more secondary peak portions.

In some aspects, the method may further comprise adjusting, based on input from the patient, a left/right balance of the primary peak portion and a left/right balance of at least one of the one or more secondary peak portions. The method may further comprise providing earphones to the patient. The earphones may comprise at least one speaker. In some aspects, the earphones, when worn by the patient, do not occlude an ear canal of the patient and allow ambient sound to reach an ear drum of the patient. In some aspects, the audio signal is transmitted to the at least one speaker. The method may be implemented over a computer network. The method may further comprise combining the audio signal with a second audio signal. The second audio signal may comprise at least one of: a music signal, a pure tone, a chord, a modulated sound, an ambient sound, and a voice signal. The method may further comprise adjusting, based on input from the patient, an intensity of the audio signal in relation to the second audio signal.

According to various aspects of the subject disclosure, a method for treating tinnitus is provided. The method may comprise providing a primary audio signal comprising a primary peak portion substantially centered at about a tinnitus frequency of a patient. The method may also comprise combining the primary audio signal with a general audio signal to generate a combined sound. The method may also comprise exposing the patient to the combined sound so that the patient hears the combined sound, to diminish a perception by the patient of tinnitus. At least one of the general audio signal and the primary audio signal may comprise a secondary peak portion substantially centered at about a frequency different from the tinnitus frequency. In some aspects, the secondary peak portion is substantially centered at about an octave or a sub-octave frequency of the tinnitus frequency. In some aspects, the secondary peak portion is substantially centered at about a harmonic or a subharmonic frequency of the tinnitus frequency.

According to certain aspects, the primary audio signal may comprise the secondary peak portion. In some aspects, at least a portion of the primary audio signal between the primary peak portion and the secondary peak portion is substantially inaudible. The method may further comprise determining the tinnitus frequency of the patient. The determining may comprise providing to the patient a range of frequencies of one or more test audio signals. The determining may also comprise, in each of a plurality of trials, receiving from the patient a selection of a frequency, chosen from the range of frequencies, approximately matching the tone of the tinnitus frequency of the patient. The determining may also comprise determining an average tinnitus frequency, based on an average of the selected frequencies from the plurality of trials.

In some aspects, the method may further comprise repeating the determining the tinnitus frequency to determine a recalibrated tinnitus frequency. The primary audio signal may further comprise a second primary peak portion that is substantially centered at about the recalibrated tinnitus frequency of the patient. The method may further comprise providing a second primary audio signal comprising a second primary peak portion substantially centered at about the recalibrated tinnitus frequency of the patient. The method may also comprise combining the second primary audio signal with a second general audio signal to generate a second combined sound. The method may also comprise exposing the patient to the second combined sound so that the patient hears the second combined sound, to diminish a perception by the patient of tinnitus. The method may further comprise combining the combined sound with the second combined sound to generate a third combined sound for treating tinnitus. The method may further comprise adjusting, based on input from the patient, a bandwidth of the primary audio signal. In some aspects, a bandwidth of the primary peak portion is up to a half octave.

In some aspects, the general audio signal may further comprise at least one of: white noise, a music signal, a pure tone, a chord, a modulated sound, an ambient sound, and a voice signal. The method may further comprise adjusting, based on input from the patient, an intensity of the primary audio signal in relation to the general audio signal. The method may also comprise adjusting, based on input from the patient, an intensity of at least one of (a) the primary peak portion, and (b) a portion of the general audio signal. The method may also comprise adjusting, based on input from the patient, a left/right balance of the primary audio signal and a left/right balance of the general audio signal. The method may further comprise providing earphones to the patient. The earphones may comprise at least one speaker. In some aspects, the earphones, when worn by the patient, do not occlude an ear canal of the patient and allow ambient sound to reach an ear drum of the patient. In some aspects, the combined sound is transmitted to the at least one speaker. The method may be implemented over a computer network.

According to various aspects of the subject disclosure, a method for treating tinnitus is provided. The method may comprise determining a tinnitus tonal key based on a tinnitus frequency of a patient. The method may also comprise providing a plurality of audio signals, each of the audio signals having a different primary tonal key from each other. The method may also comprise selecting one of the audio signals such that the primary tonal key of the selected audio signal approximately matches the tinnitus tonal key. The method may also comprise exposing the patient to the selected audio signal so that the patient hears the selected audio signal, to diminish a perception by the patient of tinnitus.

In some aspects, the method may further comprise providing a primary audio signal comprising a primary peak portion substantially centered at about the tinnitus frequency. The method may also comprise combining the primary audio signal with the selected audio signal to generate a combined sound. The method may also comprise exposing the patient to the combined sound so that the patient hears the combined sound, to diminish a perception by the patient of tinnitus. The primary audio signal may further comprise at least one of: a component of white noise, a music signal, a pure tone, a chord, a modulated sound, an ambient sound, and a voice signal.

In some aspects, the method may further comprise adjusting, based on input from the patient, an intensity of the selected audio signal in relation to the primary audio signal. The method may further comprise adjusting, based on input from the patient, a left/right balance of the selected audio signal and a left/right balance of the primary audio signal. The method may further comprise providing one or more secondary audio signals, wherein each of the one or more secondary audio signals is substantially centered at about a respective frequency different from the tinnitus frequency. In some aspects, each of at least one of the one or more secondary audio signals is substantially centered at about a respective octave or sub-octave frequency of the tinnitus frequency. In some aspects, each of at least one of the one or more secondary audio signals is substantially centered at about a respective harmonic or subharmonic frequency of the tinnitus frequency. In some aspects, at least one of the one or more secondary audio signals is substantially centered at about an octave or a sub-octave frequency of the tinnitus frequency beyond the bandwidth of the selected audio signal. In some aspects, at least one of the one or more secondary audio signals is substantially centered at about a harmonic or a subharmonic frequency of the tinnitus frequency beyond the bandwidth of the selected audio signal. In some aspects, at least a portion between one secondary audio signal and another secondary audio signal is substantially inaudible.

In some aspects, the method may further comprise adjusting, based on input from the patient, a bandwidth of at least one of the one or more secondary audio signals. In some aspects, a bandwidth of at least one of the one or more secondary audio signals is up to a half octave. The method may further comprise adjusting, based on input from the patient, an intensity of a portion of the selected audio signal in relation to at least one of the one or more secondary audio signals. The method may further comprise adjusting, based on input from the patient, an intensity of at least one of (a) a portion of the selected audio signal, and (b) one of the one or more secondary audio signals. The method may further comprise adjusting, based on input from the patient, a left/right balance of the selected audio signal and a left/right balance of at least one of the one or more secondary audio signals. The method may further comprise combining the selected audio signal with at least one of the one or more secondary audio signals to generate a combined sound for treating tinnitus.

In some aspects, the method may further comprise determining the tinnitus frequency of the patient. The determining may comprise providing to the patient a range of frequencies of one or more test audio signals. The determining may comprise, in each of a plurality of trials, receiving from the patient a selection of a frequency, chosen from the range of frequencies, approximately matching the tone of the tinnitus frequency of the patient. The determining may comprise determining an average tinnitus frequency, based on an average of the selected frequencies from the plurality of trials.

In some aspects, the method may further comprise repeating the determining the tinnitus frequency to determine a recalibrated tinnitus frequency. The method may further comprise determining a recalibrated tinnitus tonal key based on the recalibrated tinnitus frequency of the patient. The method may also comprise selecting a second one of the audio signals such that the primary tonal key of the second selected audio signal approximately matches the recalibrated tinnitus tonal key. The method may also comprise exposing the patient to the second selected audio signal so that the patient hears the second selected audio signal, to diminish a perception by the patient of tinnitus. The method may further comprise combining the selected audio signal with the second selected audio signal to generate a combined sound for treating tinnitus.

In some aspects, the selected audio signal may comprise at least one of: a music signal, a pure tone, a chord, a modulated sound, an ambient sound, and a voice signal. The method may further comprise adjusting, based on input from the patient, an intensity of a portion of the selected audio signal centered substantially at about the tinnitus tonal key in relation to at least one portion of the selected audio signal not centered substantially at about the tinnitus tonal key. The method may further comprise adjusting, based on input from the patient, an intensity of at least one of (a) a portion of the selected audio signal centered substantially at about the tinnitus tonal key, and (b) a portion of the selected audio signal not centered substantially at about the tinnitus tonal key. The method may further comprise providing earphones to the patient. The earphones may comprise at least one speaker. In some aspects, the earphones, when worn by the patient, do not occlude an ear canal of the patient and allow ambient sound to reach an ear drum of the patient. In some aspects, the audio signal is transmitted to the at least one speaker. The method may be implemented over a computer network.

According to various aspects of the subject disclosure, a computer-implemented system for treating tinnitus is provided. The system may comprise a signal module that provides a primary audio signal comprising a primary peak portion substantially centered at about a tinnitus frequency of a patient. The system may also comprise a combining module that (a) combines the primary audio signal with a general audio signal to generate a combined signal, and (b) stores the combined signal as a file in computer-readable medium. In some aspects, the file, when read in a user listening device that permits the patient to hear the combined signal, diminishes a perception by the patient of tinnitus.

In some aspects, at least one of the general audio signal and the primary audio signal may comprise a secondary peak portion substantially centered at about a frequency different from the tinnitus frequency. In some aspects, the secondary peak portion is substantially centered at about an octave or a sub-octave frequency of the tinnitus frequency. In some aspects, the secondary peak portion is substantially centered at about a harmonic or a subharmonic frequency of the tinnitus frequency. The primary audio signal may comprise the secondary peak portion. In some aspects, at least a portion of the primary audio signal between the primary peak portion and the secondary peak portion is substantially inaudible.

In some aspects, the system may be configured to perform a method of determining the tinnitus frequency of the patient. The determining may comprise providing to the patient a range of frequencies of one or more test audio signals. The determining may also comprise, in each of a plurality of trials, receiving from the patient a selection of a frequency, chosen from the range of frequencies, approximately matching the tone of the tinnitus frequency of the patient. The determining may also comprise determining an average tinnitus frequency, based on an average of the selected frequencies from the plurality of trials.

In some aspects, the method may further comprise repeating the determining the tinnitus frequency to determine a recalibrated tinnitus frequency. In some aspects, the primary audio signal may further comprise a second primary peak portion that is substantially centered at about the recalibrated tinnitus frequency of the patient. In some aspects, the signal module further provides a second primary audio signal comprising a second primary peak portion substantially centered at about the recalibrated tinnitus frequency of the patient. In some aspects, the combining module further (a) combines the second primary audio signal with a second general audio signal to generate a second combined signal, and (b) stores the second combined signal as a second file in computer-readable medium. In some aspects, the second file, when read in the user listening device that permits the patient to hear the second combined signal, diminishes a perception by the patient of tinnitus. In some aspects, the combining module further combines the combined signal with the second combined signal to generate a third combined signal for treating tinnitus.

According to certain aspects, the system may be configured to perform a method of adjusting, based on input from the patient, a bandwidth of the primary audio signal. In some aspects, a bandwidth of the primary peak portion is up to a half octave. In some aspects, the general audio signal may further comprise at least one of: white noise, a music signal, a pure tone, a chord, a modulated sound, an ambient sound, and a voice signal. In some aspects, the system may be configured to perform a method of adjusting, based on input from the patient, an intensity of the primary audio signal in relation to the general audio signal. In some aspects, the method may be configured to perform a method of adjusting, based on input from the patient, an intensity of at least one of (a) the primary peak portion, and (b) a portion of the general audio signal. In some aspects, the system may be configured to perform a method of adjusting, based on input from the patient, a left/right balance of the primary audio signal and a left/right balance of the general audio signal.

According to certain aspects, the system may further comprise the user listening device. In some aspects, the user listening device may comprise earphones. The earphones may comprise at least one speaker. In some aspects, the earphones, when worn by the patient, do not occlude an ear canal of the patient and allow ambient sound to reach an ear drum of the patient. The combined signal may be transmitted to the at least one speaker. The system may be implemented over a computer network.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIG. 11 illustrates an example of determining a tonal key of the tinnitus based on the tinnitus frequency, in accordance with one aspect of the subject disclosure.

FIG. 12 illustrates a method for treating tinnitus, in accordance with one aspect of the subject disclosure.

FIG. 14 illustrates a method for treating tinnitus, in accordance with one aspect of the subject disclosure.

DETAILED DESCRIPTION

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Figure 1A:
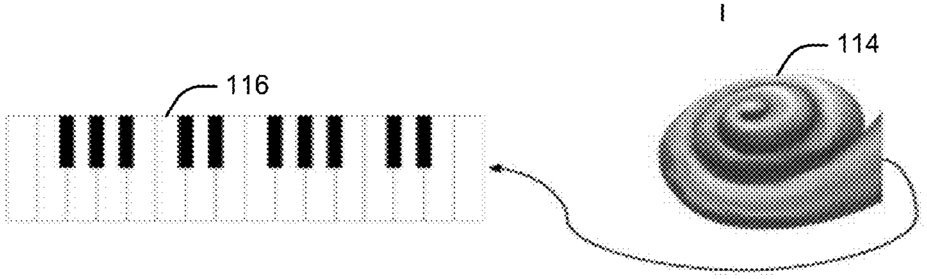
FIGS. 1A, 1B, 1C, 1D, 1E, 1F, 1G, 1H, and 1I illustrate the concept of tinnitus and approaches used for treating tinnitus, in accordance with various aspects of the subject disclosure.

FIG. 1A illustrates one representative way of describing a cochlea 114 and tinnitus. Clinically, tinnitus is the perception of sound in the absence of auditory stimulation. For example, it is hearing a ringing sound when there is no such sound. A basic discussion on how hearing works may provide an understanding of how tinnitus works. The inner ear has a structure called the cochlea 114 (so called because it looks like a snail shell). Cochlea 114 may be a fluid filled spiral structure. Sound waves may travel through the ear canal and hit the ear drum. From there, three bones of hearing may be arranged as a lever mechanism to transfer the sound energy from the ear drum to a small window at the bottom of cochlea 114 (the so-called oval window). Once this energy hits the oval window, it may start a fluid wave in cochlea 114 and travel a variable distance until it resonates with the area within cochlea 114 that corresponds with the frequency of the sound wave. Once that spot in cochlea 114 is stimulated, the nerves that connect to that specific spot may be stimulated. These nerves may then send an impulse that travels to the brain (specifically, the auditory cortex) and people may then sense or feel the sound.

Cochlea 114 may be "tono-topically" organized; that is, the frequency of a tone can be matched to a specific "topographical" location in cochlea 114. This tonotopic organization may be maintained from cochlea 114 all the way up to the auditory cortex. This organization may be compared to that of a keyboard 116 of a piano. For example, if the cochlear membrane were flattened out, the location of the low tones may be where the apex of cochlea 114 is, and the location of the high tones may be where the base of cochlea 114 is. This tonotopic organization may be maintained all the way up to the hearing part of the brain, the auditory cortex.

Many people with tinnitus hear a high pitched ring. This is because tinnitus may occur in the high frequencies; this is the location that is closest to the middle ear, and may therefore be more susceptible to damage from infection, noise damage, and general wear and tear.

Another concept to help understand why tinnitus happens deals with how the brain interprets signals coming from cochlea 114. One may expect that when there is silence, the brain may not be receiving signals from cochlea 114. This may actually not be the case. Instead, the brain may receive a constant and steady source of neuronal input from all frequencies. If electrodes were placed in the brain in a person with normal hearing, one may hear the steady crackling of spontaneous neuronal firing. The way that the brain interprets sound may be by picking up changes in this steady state of background firing.

Figure 1B:
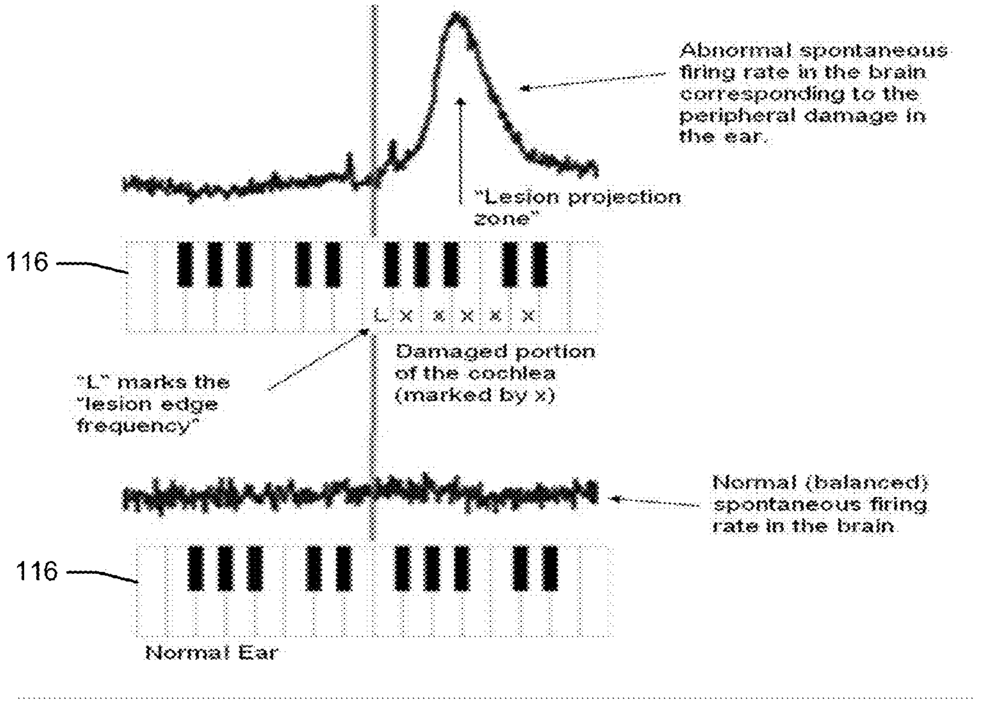

FIG. 1B illustrates an example of a situation of a damaged cochlea 114 compared to one that is not damaged. When there is damage to cochlea 114, two things may occur. First, the spontaneous firing rate in the area in the brain that corresponds with the damaged region of cochlea 114 may actually increase. This may be termed the "lesion projection zone", or the LPZ. Using the keyboard 116 as an example, if there were a set of keys on keyboard 116 that were damaged, these may then map up to the brain, and these regions may display a hyperactive spontaneous firing rate, as shown in FIG. 1B. This hyperactivity may happen fairly quickly.

The second thing that may happen is that the tones that border the damaged zone in cochlea 114 may start to become over-represented in the brain. The tone that people hear when they hear tinnitus may not correspond with the damaged zone in cochlea 114, but with the tones that just border the damaged zone. These tones have been termed the "lesion edge frequencies," and tend to correspond with the tone that people hear when they hear tinnitus. This phenomenon may occur more steadily and over time, and may be referred to as "neuroplasticity."

One way to think of neuroplasticity is that the brain may recycle unused space. "Nature abhors a vacuum." A good example of this concept is what happens when someone is blind. At birth, people have a region of the brain dedicated to sight called the "visual cortex." When someone is blind, that region of the brain may not be receiving any information. It may not be long before the neighboring regions of the brain start to take over that space and use it. Indeed, when sounds are played to someone who is blind, activation in what would normally be the visual cortex may be observed. This adaptive response may be referred to as neuroplasticity.

Tinnitus may represent a maladaptive neuroplastic response to damage in cochlea 114. Rather than have the space that corresponds to the LPZ go unused, the "lesion edge frequencies" may start to use that area and subsequently become over-represented. Hence, the hyperactive spontaneous firing rate in the LPZ may become associated with the "lesion edge frequency," and the brain may interpret it as the apprehension of sound, e.g., tinnitus.

Figure 1C:
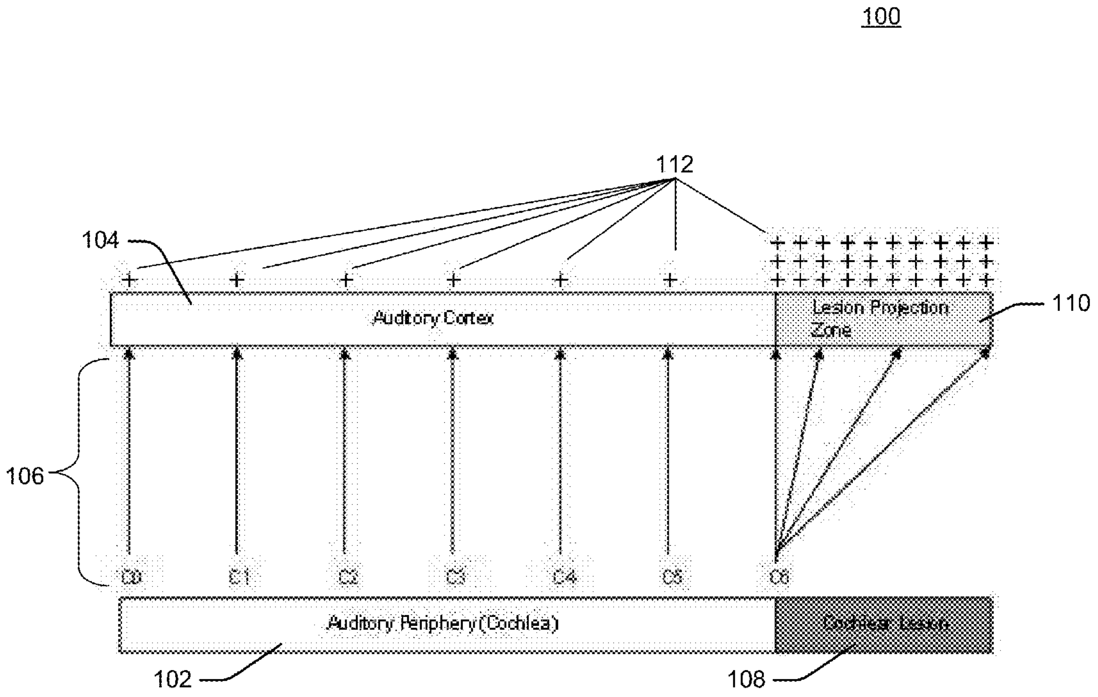

FIG. 1C illustrates an example of tinnitus model 100. Clinically, tinnitus is the perception of sound in the absence of auditory stimulation. In terms of neurophysiology, tinnitus is the consequence of a brain's response to input deprivation from auditory periphery 102 (cochlea). In a healthy auditory system, there is an ordered tonotopic frequency mapping 106 from auditory periphery 102, through the midbrain, to auditory cortex 104. When a region of the cochlea is damaged (e.g., cochlear lesion 108), the subcortical and cortical projections may adjust to this chronic lack of output (plasticity), and the tonotopic organization may be altered (e.g., C6). In auditory cortex 104, the region that corresponds to the area of cochlear damage may be termed the "lesion projection zone" (LPZ 110). After cochlear damage, neurons 112 in LPZ 110 may show two significant changes: an increase in the spontaneous firing rate and an increase in the frequency representation of neurons 112 that border the region of damage (so called 'lesion edge frequencies'). These two changes may be presumed to be the neurophysiological correlates of tinnitus. C0, C1, C2, C3, C4, C5 and C6 correspond to octave intervals of a fundamental frequency.

These changes may be explained in terms of a) loss of central inhibition on regions that are damaged and b) cortical plasticity of neighboring regions of auditory cortex 104 that are still active. Hence, tinnitus neurophysiology may be related to detrimental cortical adaptation to input deprivation from the sensory periphery.

Figure 1D:
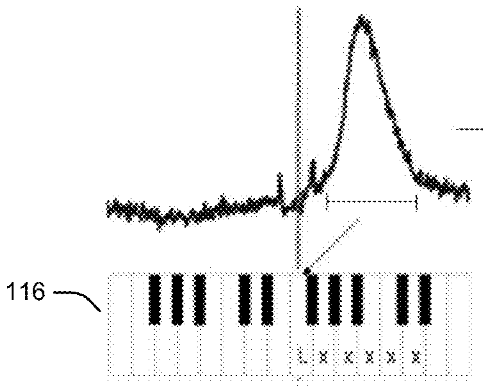
Figure 1E:
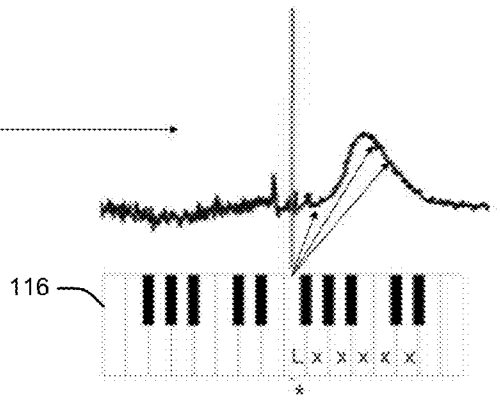

FIGS. 1D and 1E illustrates one approach to minimizing the perception of tinnitus. As it happens, the brain's maladaptive response provides a strategy to decrease the hyperactive firing rate in the LPZ 110. If a sound is presented that corresponds with the "lesion edge frequency," the spontaneous firing rate in the LPZ may diminish. For example, as shown in FIG. 1D, hyperactive "lesion projection zone" may be associated with perceived sensation of sound at the lesion edge frequency L. As shown in FIG. 1E, when frequency L is played, there may be a decrease in firing rate of the LPZ. This may correspond to tinnitus relief. This maneuver may effectively treat the physiologic counterpart to tinnitus. However, one disadvantage of this strategy may be that the internal tone (e.g., tinnitus) has been replaced with an identical external tone (at the "lesion edge frequency"), which may leave a patient no better off than before treatment.

One approach to handle this problem is to present tinnitus sufferers with a non-customized masking sound, for example white noise. In some aspects, white noise may simply be the presence of sound at all frequencies. Because white noise may always contain the "lesion edge frequency," it may always act to decrease the spontaneous firing in the LPZ. Further, the assumption is that because it contains all frequencies, the obnoxious character of the single tone at the "lesion edge frequency" gets lost in the mix and the user doesn't notice it as much.

Referring back to FIG. 1C, masking may relieve the percept of tinnitus, even if only transiently, when the masking noise is present, according to one approach. From a neurophysiology point of view, masking appears to act by relieving hyperactivity in auditory cortex 104 (and associated pathways) that accompanies peripheral deafferentation. A phenomenon of 'homeostatic plasticity' may be used to describe how the loss of peripheral afferents can cause central hyperactivity. In this approach, stimulation of the region of damage (i.e. the 'lesion-edge frequencies') may decrease this central hyperactivity. For example, masking sounds may be applied at C6, the tinnitus frequency, which may result in the sensation of tinnitus being reduced. In auditory cortex 104, this may correspond to decreased spontaneous firing rates.

Characteristics that may be optimal for masking sounds for tinnitus include maskers that a) matched the tinnitus frequency, b) which may produce narrow bands of noise that may reduce the energy delivered by the masker, and c) that may include a variable bandwidth for the masking frequencies. According to one approach, the closer a masking sound approached the narrow band that contained the tinnitus frequency, the more likely the masker was to be perceived as being equally unacceptable to the tinnitus sound. Stated simply, if the tinnitus tone is what is bothering the patient, then replacement with a similar tone at a similar volume may phenomenologically be no different than the tinnitus itself. As a result, many masking strategies still employ broadband masking noises, rather than targeted masking sounds, despite the fact that this masking strategy diverges from the most efficient masking sound from a neurophysiology point of view.

According to one approach, known as tinnitus retraining therapy (TRT), tinnitus annoyance is a product of neural networks that correlate the percept of tinnitus with the limbic system. Evidence suggests that disadvantageous neural networks involving the limbic system develop in response to tinnitus. However, these neural networks are not an obligatory response, as clinically, only 12-25% of those with tinnitus experience a negative emotive response to the tinnitus precept. The basic mechanism of TRT is to introduce 'habituation' to the tinnitus precept. Patients are given masking devices that provide only 'partial masking.' That is, patients are able to hear the masking sounds, but they are also able to perceive the tinnitus. In TRT jargon, this level of masking is termed the "mixing point." Proponents of TRT insist that access to the tinnitus precept is essential to successful therapy. Through the course of therapy, which usually lasts around 18 months, subjects are given ear-level masking devices (that cost around $1500 each) and are enjoined with multiple counseling sessions, all aimed at 'habituation' to the tinnitus precept.

Patients who have success with TRT do not lose their consciousness of tinnitus. Rather, their quality of life improves as their annoyance level to the tinnitus precept decreases. The clinical success of TRT may be secondary to remodeling of the neural networks that conjoin the auditory cortex with the limbic system in the context of tinnitus. However, there is also evidence that the subjective "loudness" of tinnitus decreases during the course of TRT, which indicates that there are changes in the auditory pathways as well. Hence, the relative contribution of remodeling of the limbic system vs. the auditory neural pathways to the therapeutic benefit of TRT is unclear.

Further elucidation of the connection between the limbic system and tinnitus may be made by examining the "non-classical" auditory pathways. Here, complex interactions via subcortical processing centers may contribute not only to the tinnitus precept, but to the maladaptive emotional response to tinnitus. Imaging studies in chronic tinnitus patients demonstrate striking structural changes in the thalamus, the relay center between the auditory cortex (via corticofugal connections), the auditory periphery (via ascending pathways from the inferior colliculus) and the limbic system. That the limbic system and the auditory system are connected makes sense from an evolutionary viewpoint; certain sounds directly stimulate autonomic responses (i.e. to alert to danger). Interestingly, these autonomic responses can be positive as well as negative, as is the case with music.

In some approaches, music may be applied as a masking medium for tinnitus. Because music may be mediated through the auditory neural pathways, music may mask the tinnitus precept. Music may also have clear associations with the limbic system, likely through thalamic 'non-classical' pathways. Even passive listening to pleasant music can positively stimulate structures of the limbic system and elicit pathways associated with pleasant emotive states. Indeed, it has been argued that music accesses the brain through subcortical connections in such a way that it can be classified as a "reflex."

In one approach, a music signal is spectrally adjusted to conform to the basic audiometric features of the tinnitus sufferer, such that the frequency profile of the music is amplified in regions of hearing loss and attenuated in regions of normal hearing. According to this approach, music may work better than other signals because it allows for intermittent masking of the tinnitus; as music reaches crescendos, the tinnitus is masked, whereas when it softens, the tinnitus percept emerges. This is correlated to the concept of 'partial masking' espoused by proponents of the TRT approach. It is unclear to what extent the spectral manipulation of the music contributes to user acceptability or more importantly, to cortical plasticity.

Specific elements of music can be refined for specific therapeutic approaches. Music perception, as opposed to general auditory functions, involves the 'tonal encoding of pitch.' Pitch may be related to the acoustic property of frequency, but may differ from frequency in that it is a perceived characteristic of a sound, rather than the pure frequency encoding of the same.

Even though certain tones may be distant in terms of frequency, they can be perceived as being related via pitch. For many years, it was thought that pitch was essentially learned. This is partly accurate, in as much as the intervals within a given 'pitch space' are culturally determined. For instance, in western music, a heptatonic scale with seven major notes (keys or chroma) define the 'pitch space.' However, other cultures express music in a pentatonic scale, such as in Celtic folk music. Hence intervals within a given 'pitch space' may be culturally defined, and therefore learned.

While intervals within a 'pitch space' may be culturally determined, the construct of a 'pitch space' may not be. Regardless of the cultural origins of the music, the 'pitch space' construct may be constant and may constitute a foundation for musical syntax. Furthermore, this 'pitch space' may be defined in octave intervals. According to certain aspects, an "octave" is an interval between one musical pitch and another with either half or double its frequency. Note here that the term "octave" may be a misnomer for scales other than the heptatonic scale. The culturally-independent definition of this relationship may be mathematical; a frequency ratio of two tones that is 2:1 or 1:2. Notes that are an octave apart entail a perception of "sameness," regardless of the cultural origin of the music. This phenomenon may be referred to as "octave generalization" or the "octave circularity of pitch," and may describe the ability to discern the perceived "sameness" between relational aspects of tones in a given 'pitch space.'

Another aspect about the octave is that octave frequencies of a fundamental frequency may be at octave intervals (i.e., $2^n$ multiples of the fundamental frequency where a positive n integer indicates a number of intervals above the fundamental frequency and a negative n integer indicates a number of intervals below the fundamental frequency). Hence, when a string instrument plays at 400 Hz, the resonant frequencies of 800 Hz (the first octave with n=1), 1600 Hz (the second octave with n=2), and onward, may also be transmitted. According to various aspects of the subject disclosure, if these higher octaves are played in the absence of the fundamental frequency, the fundamental frequency may still be perceived, and regions of auditory cortex 102 that tonotopically map to this fundamental frequency may be activated. This phenomenon may be referred to as perception of the "missing fundamental."

Figure 1F:
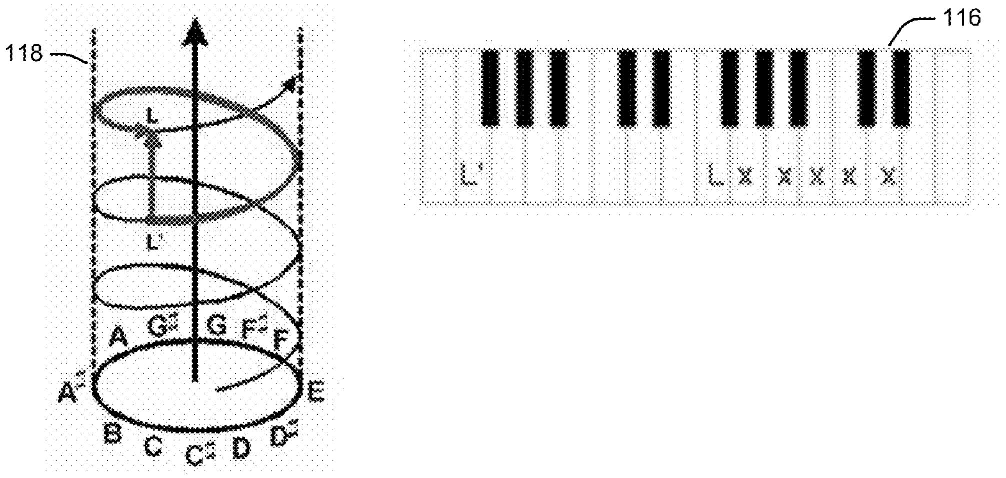

FIGS. 1F, 1G, 1H, and 1I illustrate an example of octave therapy used for treating tinnitus, in accordance with various aspects of the subject disclosure. The basis of octave therapy may be the neuroanatomical organization of octave perception. In Western musicology, there are 12 distinct notes that are defined before the pattern repeats itself. Interestingly, in different cultures, there may be a different number of "defined keys", but the octave relationship is constant. It turns out that the brain is also organized this way. There is a special part of the brain that processes pitch which may be referred to as a pitch cortex 118 and may be organized like a helix, as shown in FIG. 1F.

In FIG. 1F, even though L' and L may be 12 notes away, in pitch cortex 18, they are only one spiral away from each other. It is in pitch cortex 118 that the neuroanatomical can be observed to correlate to octave perception. In some aspects, such a relationship may be a basis for octave therapy. It is interesting that when patients are being tested to identify their tinnitus tone, they may sometimes mistake their true tinnitus tone for the tone an octave below. This phenomenon may be referred to as "octave confusion." The reason why people do this can be explained by the organization of pitch cortex 118.

According to various aspects of the subject disclosure, the relationship noted above may be utilized to create a masking strategy that enables the stimulation of octave or sub-octave tones to the tinnitus frequency (e.g., the "leading edge frequency") that avoids the noxious quality that may result if the tinnitus frequency were stimulated alone. In some aspects, octave therapy involves the stimulation of the lesion edge frequency and its sub-octave tones (i.e. tones that are in octave intervals lower than the tinnitus frequency) to decrease hyperactivity in the LPZ via pitch cortex 118.

Figure 1G:
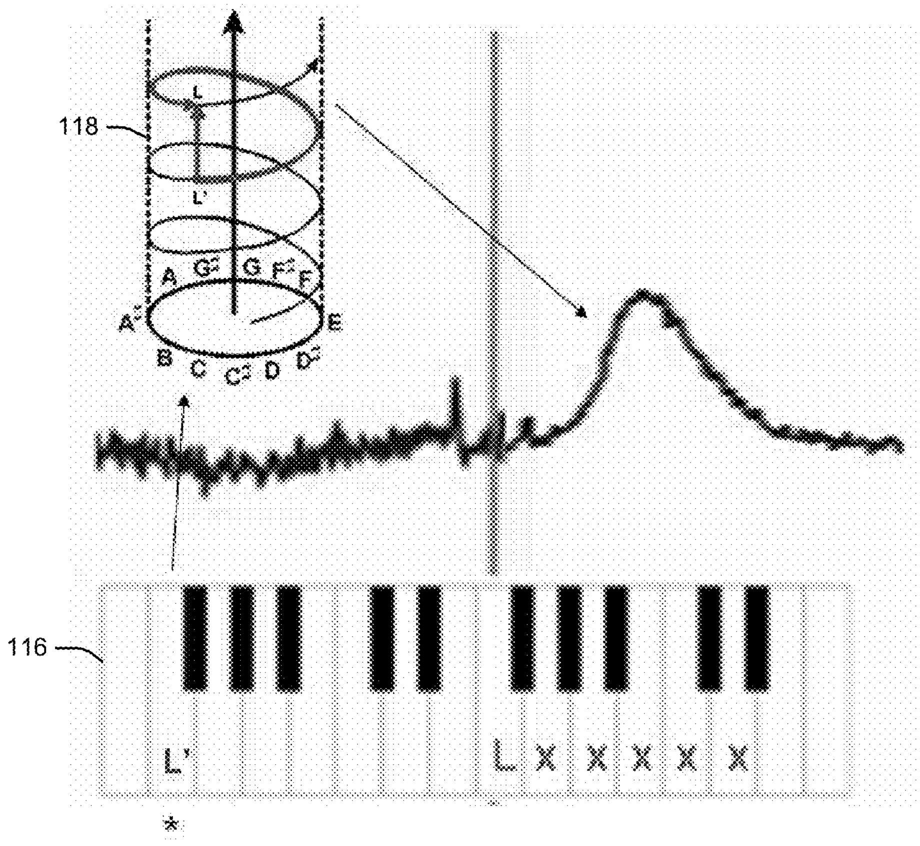

As shown in FIG. 1G, if the first sub-octave tone (L') to the leading edge frequency L is stimulated, a similar decrease in LPZ hyperactivity may be achieved as if L were stimulated alone, in accordance with various aspects of the subject disclosure. This concept can be extended to further sub-octaves or octaves as well (e.g., L", etc.).

Figure 1H:
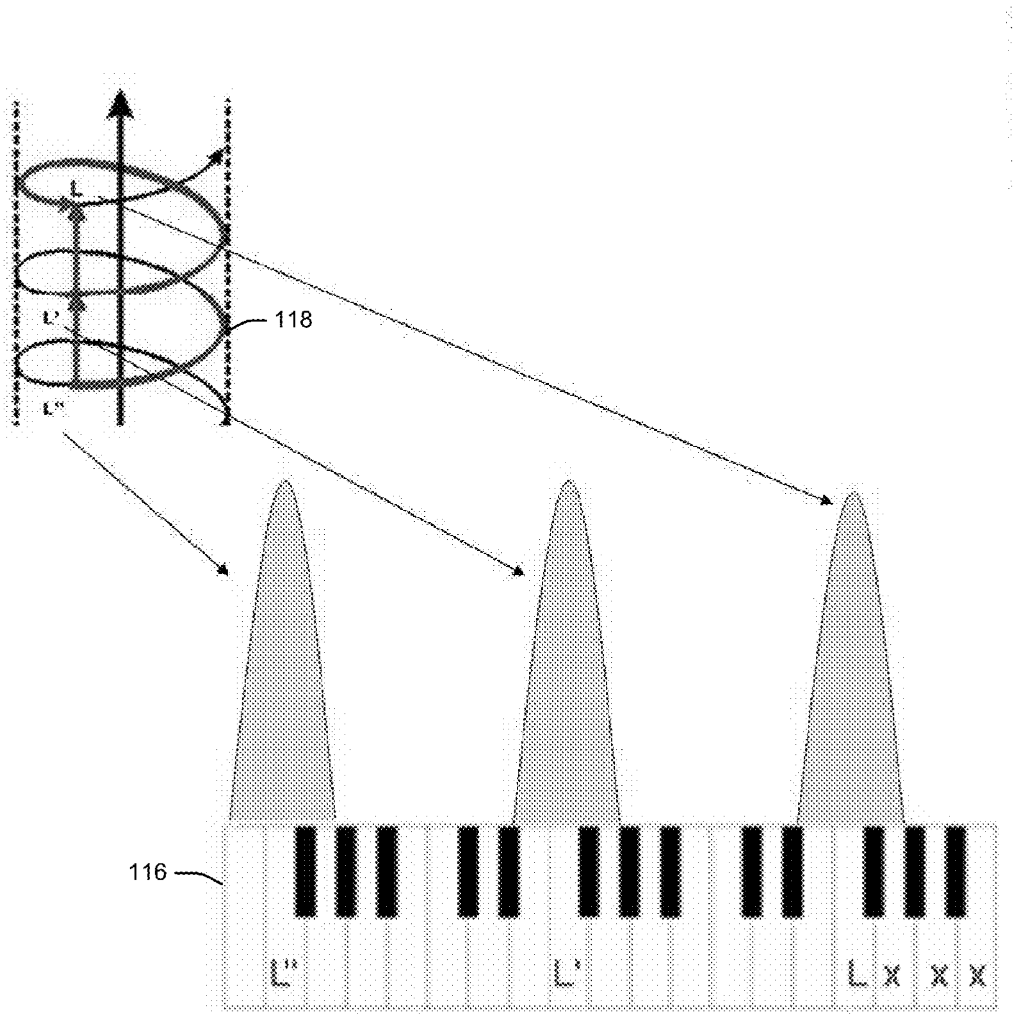

In some aspects, various combinations of octave and/or sub-octave tones may lead to a masking sound that is both comfortable to listen to and provides a therapeutic benefit. As shown in FIG. 1H, narrow bands of noise may be delivered at octave or sub-octave intervals to the tinnitus frequency (e.g., the leading edge frequency L). This masking strategy utilizes the structure of pitch cortex 118, allowing for maximal masking energy with minimal sound output. The result may be a very comfortable yet highly effective masking sound.

In some aspects, a tone comprises a band of structured noise that may surround the tinnitus frequency and its octaves or sub-octaves. Each octave masking sound may be different for each person. An online protocol is provided that takes into account the tinnitus frequency, the right-left balance, and the difference in hearing from low to high tones to create a customized octave masking file for each user. In some aspects, the end result may be a file that sounds much like various soothing sounds (e.g., running water in the background). In some aspects, use of these customized masking sounds may provide patients the feeling of balance in their minds, as if they are not listening to anything at all.

Figure 1I:
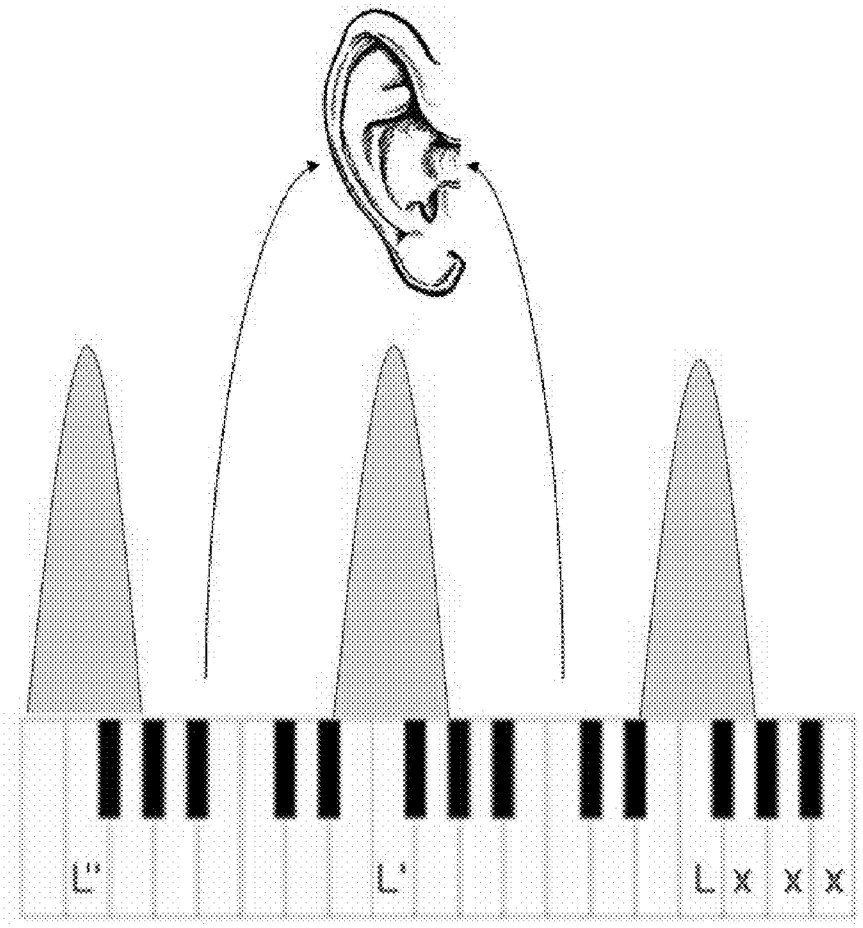

Another drawback of traditional masking strategies may be that when patients are listening to maskers, they may not very well hear anything else. Because octave masking may only target regions of the hearing spectrum that involve the tinnitus frequency and its octaves or sub-octaves, the remaining portions of the hearing spectrum may be allowed to pass through to the ear. This may enable people to use their therapeutic sound files during the course of their everyday activities. In some aspects, this pass-through phenomenon may be utilized with earphones, such as AIRDRIVE TECHNOLOGY earphones. As shown in FIG. 1I, octave masking may only occupy portions of the hearing spectrum that is necessary to achieve maximum tinnitus relief, leaving the rest of the frequency space open so that ambient sounds can pass through and reach the ear, in accordance with various aspects of the subject disclosure.

Figure 2:
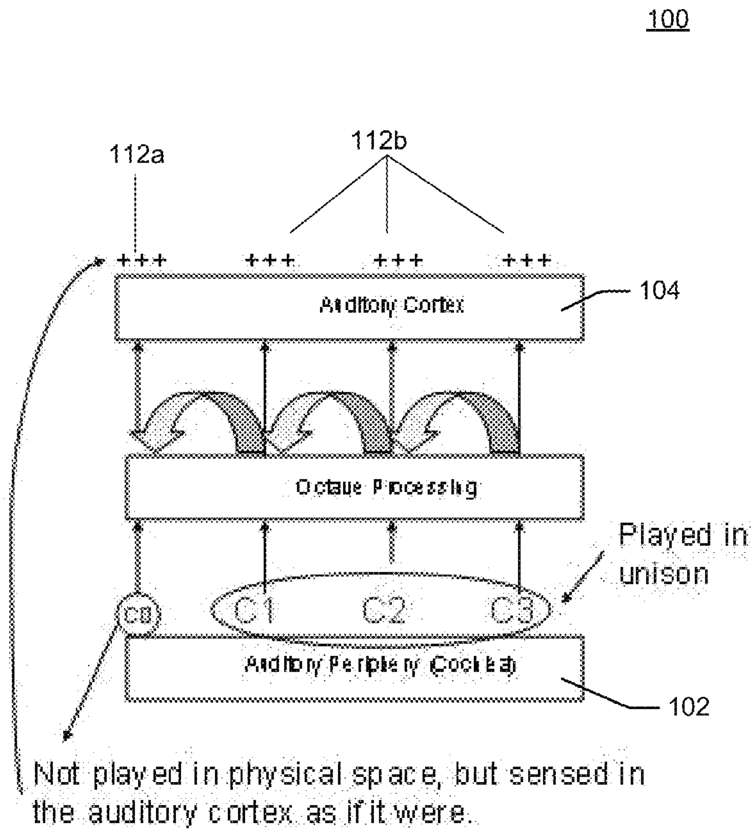
FIG. 2 illustrates an example of a missing fundamental, in accordance with one aspect of the subject disclosure.

FIG. 2 illustrates an example of a missing fundamental, in accordance with one aspect of the subject disclosure. In the missing fundamental (e.g., at C0), if the octaves above the fundamental frequency (e.g., C1, C2, C3) are played, neurons 112*a* with a central frequency that correspond to the missing fundamental fire as well, even if there is no physical sound presented to auditory periphery 102.

Evidence of pitch specific neural substrates has been found in both the brainstem and auditory cortex 104. The ventral division of the medial geniculate nucleus (MGN) of the thalamus has stacked neuron layers where frequency representation may progress in intervals of approximately one octave across layers. Such representations may be mediated by the ventrolateral lemniscus of the inferior colliculus. This structure has a unique helical structure that runs orthogonal to the tonotopic structure of the IC, a structure that is reminiscent of the pitch helix described in music theory.

Pitch processing may occur in auditory cortex 104. "Peridotopic" maps may run orthogonal to tonotopic maps in auditory cortex 104. There may also be a dedicated "pitch center" in the "belt region" of the auditory cortex.

Given that people may have been hardwired to perceive octaves as the same sound, and that this is recapitulated in tinnitus patients in the "octave confusion" phenomenon, the octave construct may be exploited in therapeutic strategies for tinnitus rehabilitation, in accordance with various aspects of the subject disclosure. A method is provided that may establish the "chroma" (e.g., key) of a patient's tinnitus by reducing the tinnitus frequency to its fundamental pitch in the musical range. This method may then introduce a pedagogical approach that reinforces the octave relationships that exist in a continuum between the tinnitus frequency and the lower octaves that define the "tinnitus chroma."

One approach may be reduced to the following phrase, "Cells that fire together, wire together." According to this approach, repeated and synchronized simulation of interconnected cells may create and strengthen a "neural network." It is relevant in the context of tinnitus because it pertains to the possibility of harnessing synaptic plasticity of neuronal inputs that may alter the tinnitus precept. If tinnitus is the result of maladaptive cortical plastic changes, these may be remedied through structured learning.

According to various aspects of the subject disclosure, one way of building stable and efficient neural networks (i.e. auditory cortex remodeling), and thus to treat tinnitus, may be to evoke multiple neurons at different levels of the auditory system; that is, via heterotopic connections that include cortico-cortical and thalamo-cortical interconnections. The connections that govern musical syntax and pitch perception may be precisely these types of heterotopic connections. Hence, tinnitus rehabilitation may involve harnessing the power of music by amplifying and strengthening its most basic, yet most robust, neural interconnections in the midbrain and cortex; namely, octave relationships.

In some aspects, a method that involves active musical training, not just passive music perception, is provided. By introducing a subject to a pedagogy that reinforces these relationships through repetition and multi-sensory exercises, a measure of auditory cortical reorganization capable of mitigating the tinnitus precept can be achieved. According to some aspects, an element of attentiveness to the therapeutic stimulus may be needed.

In some aspects, octave tinnitus therapy (OTT) is provided. According to one aspect of the subject disclosure, OTT may comprise various elements, including induction of tetanic inhibition via long term masking, induction of cortical reorganization driven by octave training, and induction of limbic reassignment through musical therapy.

Figure 3:
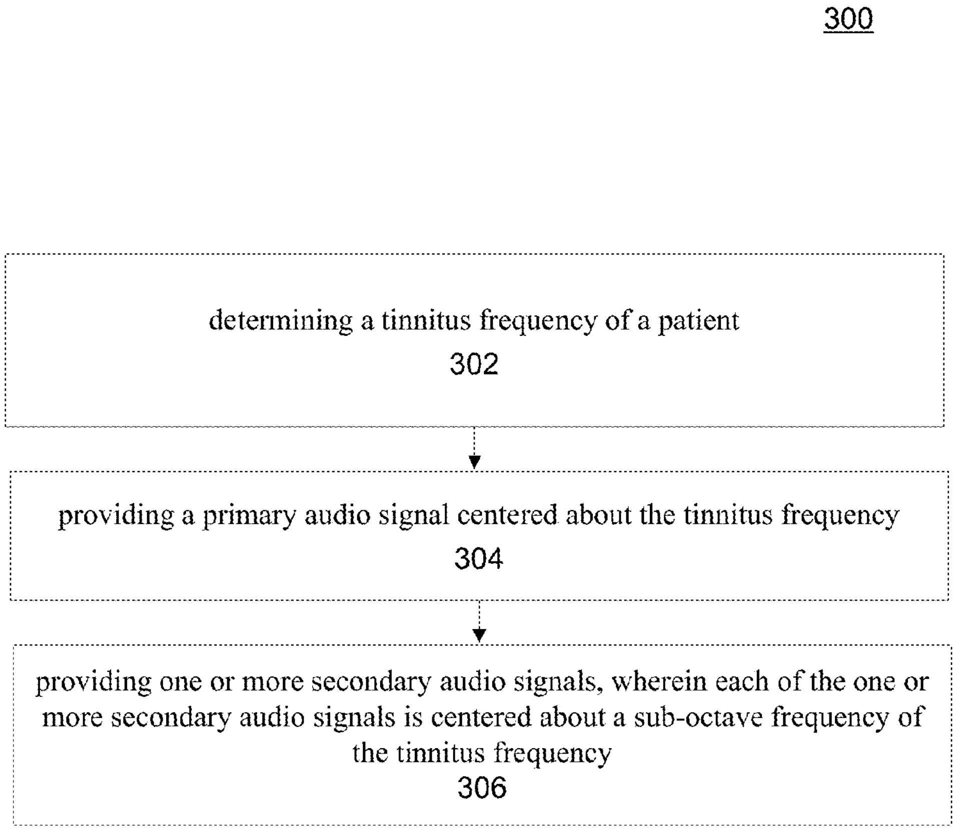
FIG. 3 illustrates a method for treating tinnitus, in accordance with one aspect of the subject disclosure.
Figure 4:
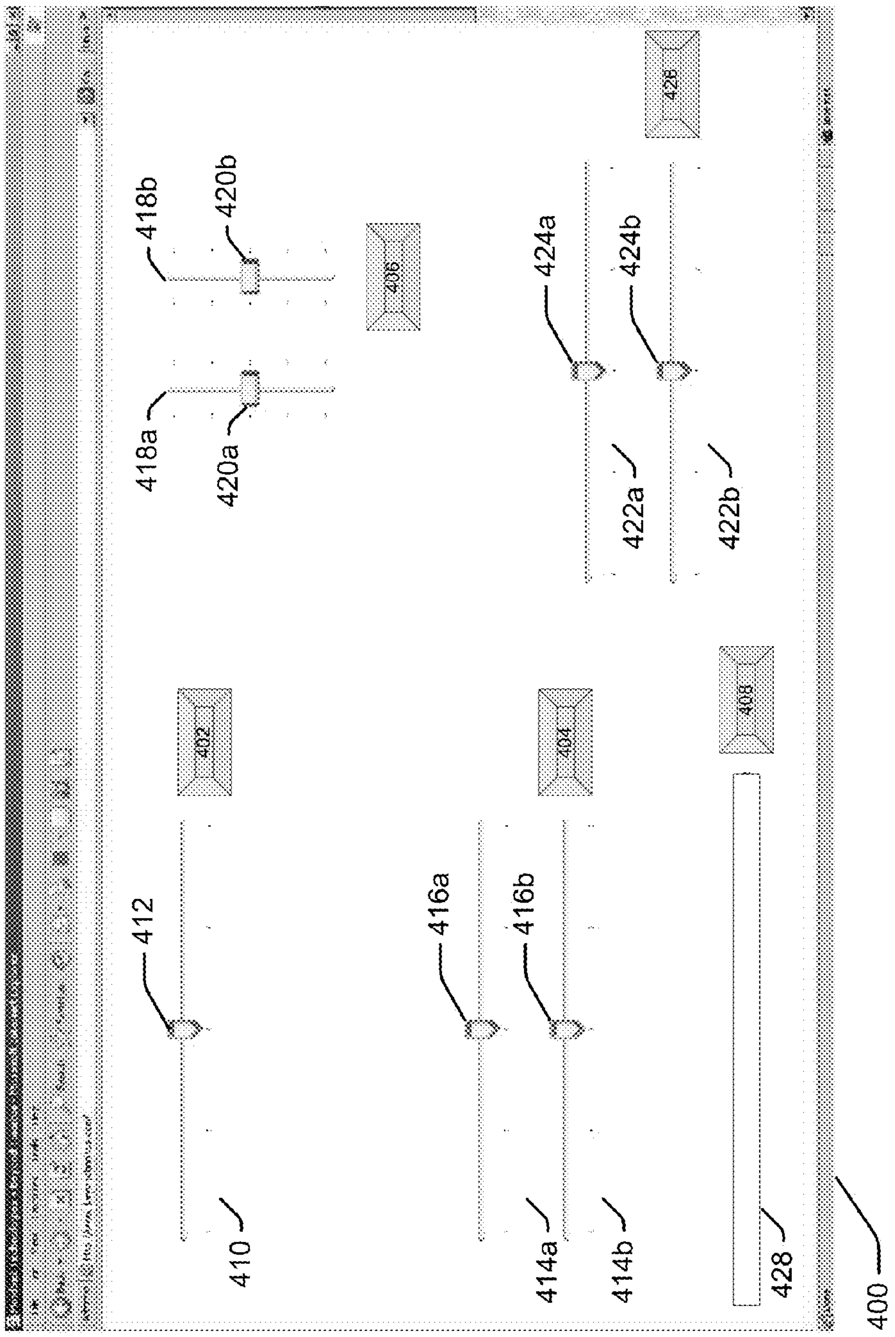
FIG. 4 illustrates an example of an internet-based approach for treating tinnitus, in accordance with one aspect of the subject disclosure.

FIG. 3 illustrates a method 300 for treating tinnitus, in accordance with one aspect of the subject disclosure. Method 300 comprises determining a tinnitus frequency of a patient (302). The tinnitus frequency of a patient may be determined in a number of ways. For example, FIG. 4 illustrates an example of an internet-based approach for treating tinnitus, in accordance with one aspect of the subject disclosure. A method of treating tinnitus, using an internet-based approach, may provide convenience and interactivity for a patient suffering from tinnitus. For example, patients may log onto website 400 to diagnose and treat tinnitus. An internet-based approach to treating tinnitus may provide many benefits including ease of use, convenience, a single source of information, customized storage of patient profile settings, community based knowledge, quick updates, and interactivity. For example, use of a questionnaire with parameters such as anxiety, depression, and insomnia may help automate specific therapeutic options and information.

In some aspects, a patient may create a profile according to website 400. Website 400 may include patient information (e.g., in a database) pertaining to the treatment of tinnitus, including the patient's tinnitus frequency, hearing levels based on intensity, right/left hearing balance, progress indicators such as graphs and illustrations with respect to the patient's condition, or any other information related to the treatment of tinnitus. Website 400 may also include questionnaires, surveys, tests, or other material to obtain information about the patient for treatment, diagnosis, or other purposes.

In some aspects, a patient may utilize website 400 to determine his/her tinnitus frequency. The patient may be provided with a range of frequencies of one or more test audio signals. For example, website 400 may comprise tinnitus frequency tuner 410. Tinnitus frequency tuner 410 may comprise slider 412 and button 402. Depending on the position of slider 412, a different tone corresponding to a certain frequency may be played on the website (e.g., test audio signals). The patient may adjust slider 410 in either direction (such as to the right or to the left) to "sweep" through the range of frequencies provided in order to hear the range of tones corresponding to the range of frequencies. In some aspects, the range of frequencies is between about 50 Hz and 20,000 Hz. In some aspects, the upper limit of the range of frequencies may be greater than or equal to about 20,000 Hz. In some aspects, the lower limit of the range of frequencies may be less than or equal to about 50 Hz. As the patient adjusts slider 410, the patient may select one frequency from the range of frequencies that approximately matches the tone of the tinnitus that the patient is suffering from. The patient may then submit and save this information on website 400, for example, by activating button 402. In some aspects, this process may be repeated one or more times until a suitable average selected frequency is obtained. The average selected frequency may then be determined to be the tinnitus frequency of the patient.

Turning back to FIG. 3, method 300 also comprises providing a primary audio signal centered about the tinnitus frequency (304). Method 300 also comprises providing one or more secondary audio signals, wherein each of the one or more secondary audio signals is centered about a sub-octave frequency of the tinnitus frequency (306). In some aspects, by providing a primary audio signal centered about the tinnitus frequency, in combination with one or more secondary audio signals centered about sub-octave frequencies of the tinnitus frequency, a masking sound may be created for treating a patient's tinnitus. In some aspects a single audio signal instead of separate primary and secondary audio signals may be provided, where the single audio signal comprises a primary peak portion (e.g., corresponding to a primary audio signal) that is substantially centered at about a tinnitus frequency of the patient, and one or more secondary peak portions (e.g., corresponding to one or more secondary audio signals), each of which is substantially centered at about a frequency different from the tinnitus frequency. In some examples, the secondary peak portions of the single audio signal may not have to be centered at about an octave or sub-octave frequency. Rather, the secondary peak portions of the single audio signal may be at any frequency lower or higher than the tinnitus frequency to provide a suitable masking effect.

Figure 5:
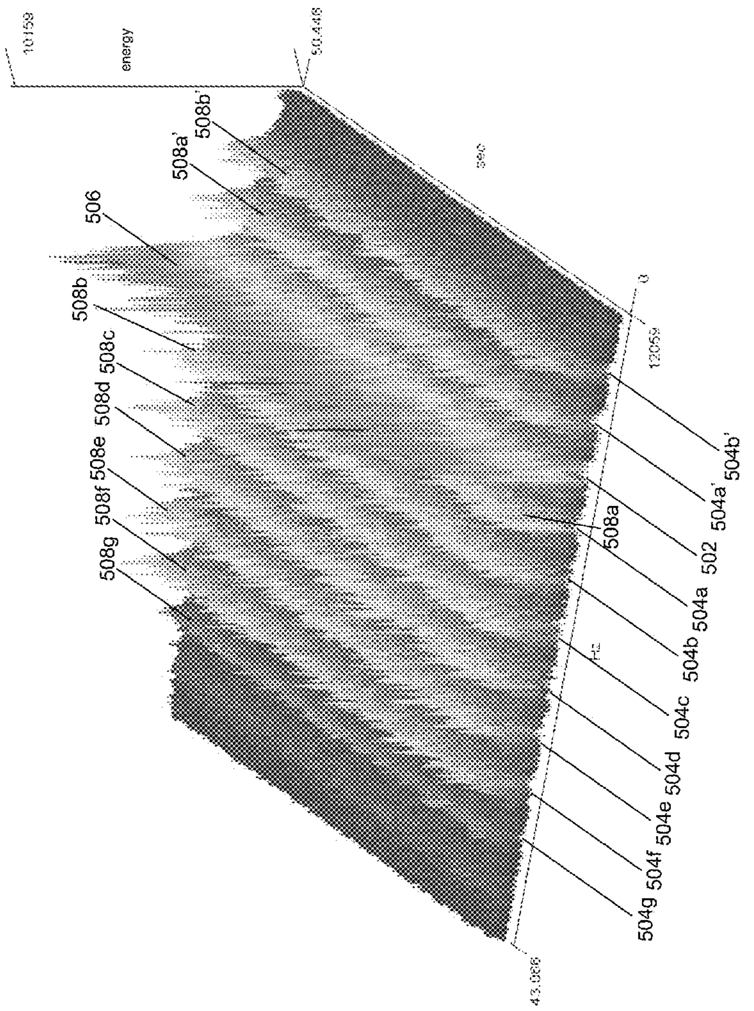
FIG. 5 illustrates an example of a masking sound, in accordance with one aspect of the subject disclosure.

FIG. 5 illustrates an example of masking sound 500, in accordance with one aspect of the subject disclosure. Masking sound 500 may comprise primary audio signal 506 and one or more secondary audio signals 508 (e.g., 508*a*, 508*b*, 508*c*, 508*d*, 508*e*, 508*f*, 508*g*, 508*a*', 508*b*'). In some aspects, induction to OTT may be started through tetanic inhibition. Targeted (e.g., narrowband) masking may be implemented at tinnitus frequency 502 in order to drive a tetanic inhibition of the cortical hyperactivity that is driving the tinnitus precept. For example, primary audio signal 506 may be provided, centered about tinnitus frequency 502. This "induction phase" may act to prime the auditory cortex (e.g., auditory cortex 104 of FIG. 1) for reorganization, but also to give the patient the psychological benefit of knowing that tinnitus relief is possible. In some aspects, narrowband masking may be produced from and/or in combination with octave masking. While a single narrowband noise applied at tinnitus frequency 502 may sound harsh and may be abrasive, the addition of multiple narrowband channels of audio at octave intervals of tinnitus frequency 502 (e.g., octave frequencies 504*a*, 504*b*, 504*c*, 504*d*, 504*e*, 504*f*, 504*g*, 504*a*', 504*b*') may give masking sound 500 more depth. For example, secondary audio signals 508 may be provided, where each of the secondary audio signals is centered about an octave frequency 504 of tinnitus frequency 502. In some aspects, secondary audio signals 508 may comprise an individual audio signal centered about an octave frequency 504 of tinnitus frequency 502. In some aspects, secondary audio signals 508 may comprise multiple audio signals centered about various octave frequencies 504 of tinnitus frequency 502.

Octave frequencies 504 comprise one or more sub-octave frequencies (octave frequencies lower than tinnitus frequency 502 such as sub-octave frequencies 504*a*, 504*b*, 504*c*, 504*d*, 504*e*, 504*f* and 504*g*) and/or one or more supra-octave frequencies (octave frequencies greater than tinnitus frequency 502 such as supra-octave frequencies 504*a*' and 504*b*'). In some aspects, supra-octave frequencies may be referred to as octave frequencies. Sub-octave frequency 504*a* may be referred to as the first sub-octave frequency, sub-octave frequency 504*b* may be referred to as the second sub-octave frequency, and sub-octave frequency 504*c* may be referred to as the third sub-octave frequency, etc. Any number of combinations between primary audio signal 506 and secondary audio signals 508 may be used in generating masking sound 500. In some aspects, only primary audio signal 506 may be used to generate masking sound 500. In some aspects, only secondary audio signals 508 may be used to generate masking sound 500. In some aspects, both primary audio signal 506 and any number of secondary audio signals 508 may be used to generate masking sound 500.

According to various aspects of the subject disclosure, primary audio signal 506 may comprise white noise, a music signal, one or more pure tones, one or more chords, one or more modulated sounds (e.g., amplitude modulated sounds), one or more ambient sounds, a voice signal or a combination thereof. In some aspects, secondary audio signals 508 may comprise white noise, a music signal, one or more pure tones, one or more chords, one or more modulated sounds, one or more ambient sounds, a voice signal or a combination thereof. For example, primary audio signal 506 and/or secondary audio signals 508 may be a combination of three musical notes, like a chord, a sample recording of rain, or other soothing sounds. In some aspects, ambient sound may be given its ordinary meaning. In some aspects, ambient sound may refer to a recording of a natural sound such as sound of the ocean, rainfall, jungle, rainforest, waterfall, rain, wind, or any other soothing sounds.

According to various aspects of the subject disclosure, the bandwidth of primary audio signal 506 and/or secondary audio signal 508 may be adjusted according to a comfort level as defined by the patient. For example, in FIG. 4, website 400 may comprise bandwidth tuner 414 (e.g., 414*a* for primary audio signal 506 and 414*b* for secondary audio signals 508). Additional bandwidth tuners 414 may be provided for additional audio signals. Bandwidth tuner 414 may comprise sliders 416 (e.g., 416*a* for primary audio signal 506 and 416*b* for secondary audio signals 508) and button 404. A patient may adjust the position of sliders 416 to adjust the bandwidth of either primary audio signal 506 or secondary audio signals 508 such that masking sound 500 may provide a comfort level acceptable to a patient in masking the patient's tinnitus tone. The patient may save and submit this information on website 400, for example, by activating button 404. In some aspects, the patient may be given the option to adjust the bandwidth of either primary audio signal 506 and/or secondary audio signals 508 in future sessions to account for changes in the patient's hearing and/or tinnitus.

In some aspects, the bandwidth of primary audio signal 506 may be adjusted to about ⅛, ¼, or ½ of an octave around tinnitus frequency 502. In some aspects, the bandwidth of primary audio signal 506 may range from a fraction greater than a single tone to a half octave band of primary audio signal 506 centered about tinnitus frequency 502. In some aspects, the bandwidth of each of the secondary audio signals 508 may be adjusted to about ⅛, ¼, or ½ of an octave around a respective octave frequency 504. In some aspects, the bandwidth of each of the secondary audio signals 508 may range from a fraction greater than a single tone to a half octave of the each of the secondary audio signals 508 centered about a respective octave frequency 504.

According to various aspects of the subject disclosure, primary audio signal 506 may be combined with secondary audio signals 508 to generate masking sound 500 for treating tinnitus. This approach may be referred to as octave masking, which may allow intense energy to be delivered at tinnitus frequency 502 (e.g., primary audio signal 506), but with the abrasiveness diminished by spreading the energy across lower octaves (e.g., at secondary audio signals 508), while at the same time exploiting the interconnectedness of these two regions via the pitch cortex. A further advantage is that ambient sounds outside of these bands may be allowed to reach the patient, offering diminished auditory handicap from using a long-term masking device.

According to various aspects of the subject disclosure, the intensity (e.g., volume) of primary audio signal 506 may be adjusted. Often, patients suffering from tinnitus also suffer from hearing loss. For patients with a high frequency tinnitus frequency (e.g. at about 8,000 to 20,000 Hz), the same patients may also suffer from hearing loss at these high frequencies. As a result, the actual intensity at high frequencies that the patient hears does not necessarily match the actual intensity at lower frequencies that the patient hears. In accordance with various aspects of the subject disclosure, the relative perceived intensity of primary audio signal 506 may be adjusted to match the intensity of audio signals of different frequencies.

For example, the relative perceived intensity between the intensity of primary audio signal 506 and an intensity of a calibration audio signal can be adjusted. In some aspects, the calibration audio signal may be any one of secondary audio signals 508. In some aspects, secondary audio signals 508 may comprise the calibration audio signal. In some aspects, the calibration audio signal is centered about a frequency within a bandwidth of at least one of secondary audio signals 508. The relative perceived intensity between the intensity of primary audio signal 506 and the intensity of the calibration audio signal can be adjusted in various ways. For example, referring back to FIG. 4, website 400 may comprise intensity tuner 418 (e.g., 418*a* for primary audio signal 506 and 418*b* for calibration audio signal). Additional intensity tuners 418 may be provided for additional or different calibration audio signals. Intensity tuner 418 may comprise sliders 420 (e.g., 420*a* for primary audio signal 506 and 420*b* for calibration audio signal) and button 406. Different positions of slider 420 may correspond to different intensities of either primary audio signal 506 or the calibration audio signal. In some aspects, the range of intensities provided by intensity tuner 418 may be about 0% to 100% of an intensity of either primary audio signal 506 or the calibration audio signal.

As website 400 provides a range of intensities of both primary audio signal 506 and the calibration audio signal, a patient may adjust sliders 420 to select a specific intensity of either primary audio signal 506 or the calibration audio signal to play on website 400. For example, a patient may adjust slider 420*b* in order to select an intensity of the calibration audio signal according to a comfort level as defined by the patient. The patient may then adjust slider 420*a* to select an intensity of primary audio signal 506 such that a perceived intensity of primary audio signal 506 approximately matches the intensity of the calibration audio signal. In this way, even if the patient suffers hearing loss, for example in frequencies around primary audio signal 506, the patient may still be able to select an intensity of primary audio signal 506 that is perceived to be roughly about the same intensity of the calibration audio signal. The patient may then save and submit this preference/information on website 400, for example, by activating button 406.

In accordance with various aspects of the subject disclosure, the left/right balance of primary audio signal 506 and the left/right balance of secondary audio signals 508 may be adjusted according to a subjective relative intraaural intensity of the tinnitus. For example, as shown in FIG. 4, website 400 may provide an intraaural intensity tuner 422 (e.g., 422*a* for primary audio signal 506 and 422*b* for secondary audio signals 508). Additional intraaural intensity tuners 422 may be provided for additional or different audio signals. Intraaural intensity tuner 422 may comprise sliders 424 (e.g., 424*a* for primary audio signal 506 and 424*b* for secondary audio signals 508) and button 426. A patient may adjust the positions of sliders 424 in order to adjust the intraaural intensity of either primary audio signal 506 or secondary audio signals 508. In this way, a patient may balance the hearing on both ears by moving sliders 424 to an appropriate position. For example, a patient may adjust sliders 424 to the left or right to determine and calibrate a left/right balance of either primary audio signal 506 or secondary audio signals 508. Once the patient has selected a comfortable balance, the patient may then save and submit this preference/information on website 400, for example, by activating button 426.

Figure 6:
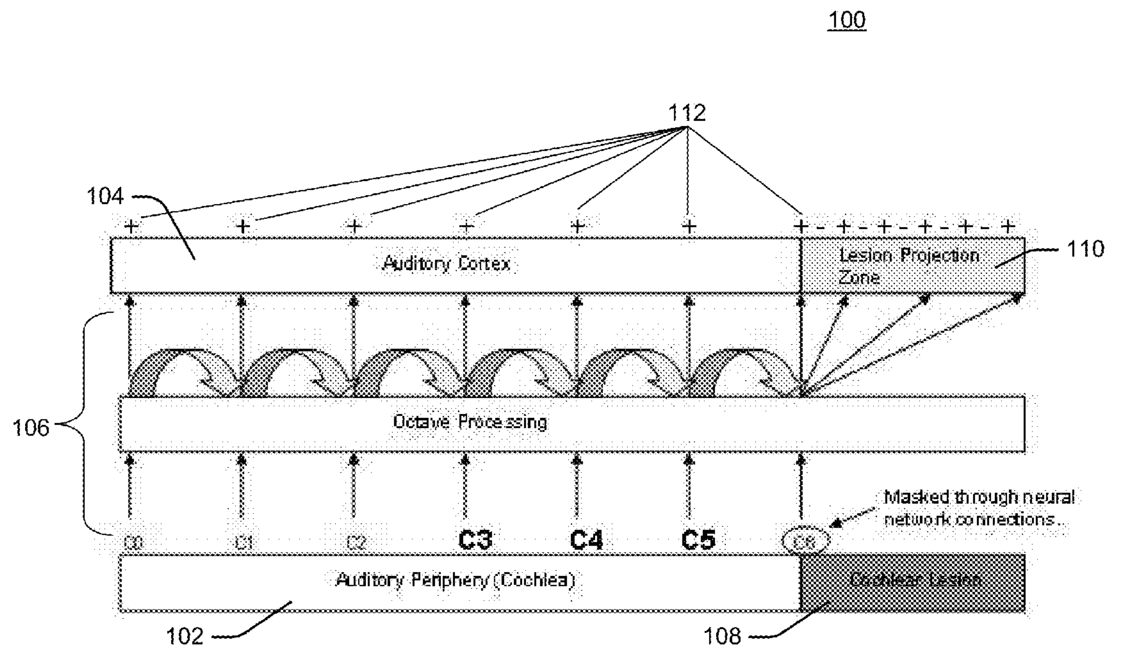
FIG. 6 illustrates an example of a tinnitus model with octave masking, in accordance with one aspect of the subject disclosure.

FIG. 6 illustrates an example of tinnitus model 100 with octave masking, in accordance with one aspect of the subject disclosure. The same neural network responsible for octave perception may be used to provide masking at tinnitus frequency (e.g., C6). Musical training may be used to enable the mind to extrapolate octave frequencies of the fundamental frequency in order to stimulate the tinnitus frequency, thereby producing a masking effect. For example, audio signals present at the octaves of the tinnitus frequency (e.g., at C0, C1, C2, C3, C4 and C5) may produce a masking effect at the tinnitus frequency. As shown, the number of neurons 112 “firing” at C6 can be reduced as compared to FIG. 1.

According to various aspects of the subject disclosure, musical training may be introduced via octave perception and association. In some aspects, the patient’s tinnitus frequency may initially be determined, for example, using the techniques described above. Once this is done, the fundamental “tinnitus chroma” for the patient may be defined. Multiple modalities may be used in order to allow the patient to become familiar with these octave constructs, including multisensory exercises. Psychoacoustic studies have shown the pitch range of humans to extend to about 5 kHz, a range that may be below the tinnitus frequency of some users. In these circumstances, extensive training may be provided in order to facilitate a neural link between tinnitus frequency and its correlate sub-octave that is within the pitch range. Eventually, the patient may learn to associate the tinnitus frequency not as a single tone, but as member of a pitch class that is unique to the patient.

From extensive exercises built on bolstering “octave generalization,” the patient may graduate to other well defined consonant constructions, for example, thirds and fifths. This training may be a stepping stone bridging the precept of a “pitch class” to “pitch relations.” Finally, this musical training may expand into the analysis of more complex musical constructions. In some aspects, computer generated music may be used that may be pseudorandomly generated based on consonant constructions within the users “tinnitus chroma.”

Figure 7:
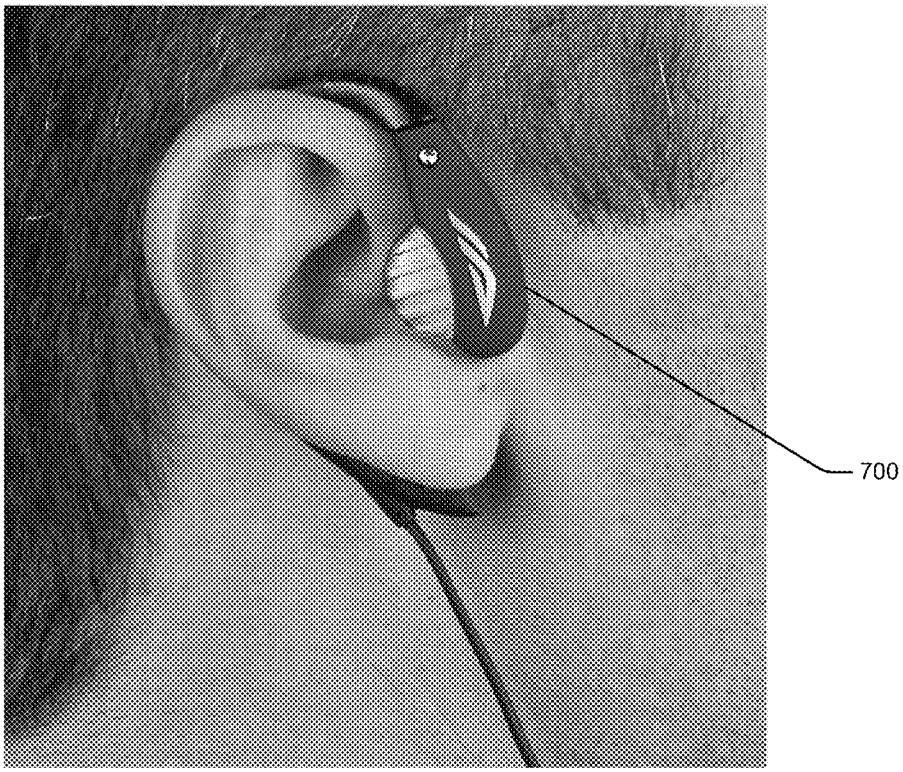
FIG. 7 illustrates an example of earphones that may be used for treating tinnitus, in accordance with one aspect of the subject disclosure.

Referring to FIGS. 4, 5 and 7, masking sound 500 may be made available for download from website 400. For example, after website 400 collects information pertaining to the patient’s tinnitus (e.g., patient’s tinnitus frequency, comfort in terms of the bandwidth and/or intensity of primary and secondary audio signals, etc.), website 400 may generate masking sound 500 by combining primary audio signal 506 and secondary audio signals 508. Masking sound 500 may be in a way, wmv, mp3, midi, or any other suitable audio format. The patient may then download masking sound 500 from website 400. Masking sound 500 may also be downloadable into an audio device. In this way, the patient may listen to masking sound 500 either on a computer or on any other suitable audio device for playing back audio files. Masking sound 500 may be played with earphones 700, for example, for masking for several hours a day. Earphones 700 may comprise one or more speakers that sit outside the ear canal of the patient when the earphones are worn by the patient. For example, earphones 700 may be INAIR TECHNOLOGY or AIRDRIVE TECHNOLOGY earphones, which have devices that allow delivery of sound through tragal transmission, allowing the external auditory canal to be open for detection of ambient sounds. This means that masking can occur throughout the day, at work, during driving, and during most daily activities without distracting from ambient sounds.

Figure 8:
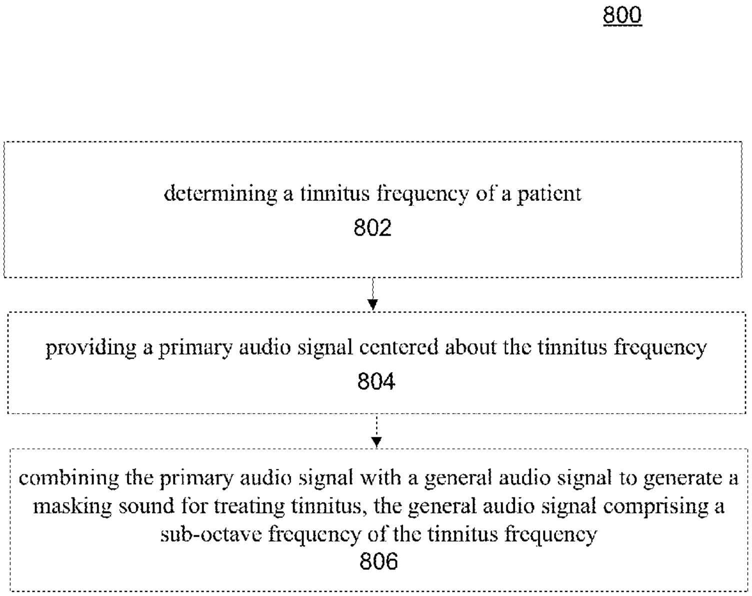
FIG. 8 illustrates another method for treating tinnitus, in accordance with one aspect of the subject disclosure.
Figure 9:
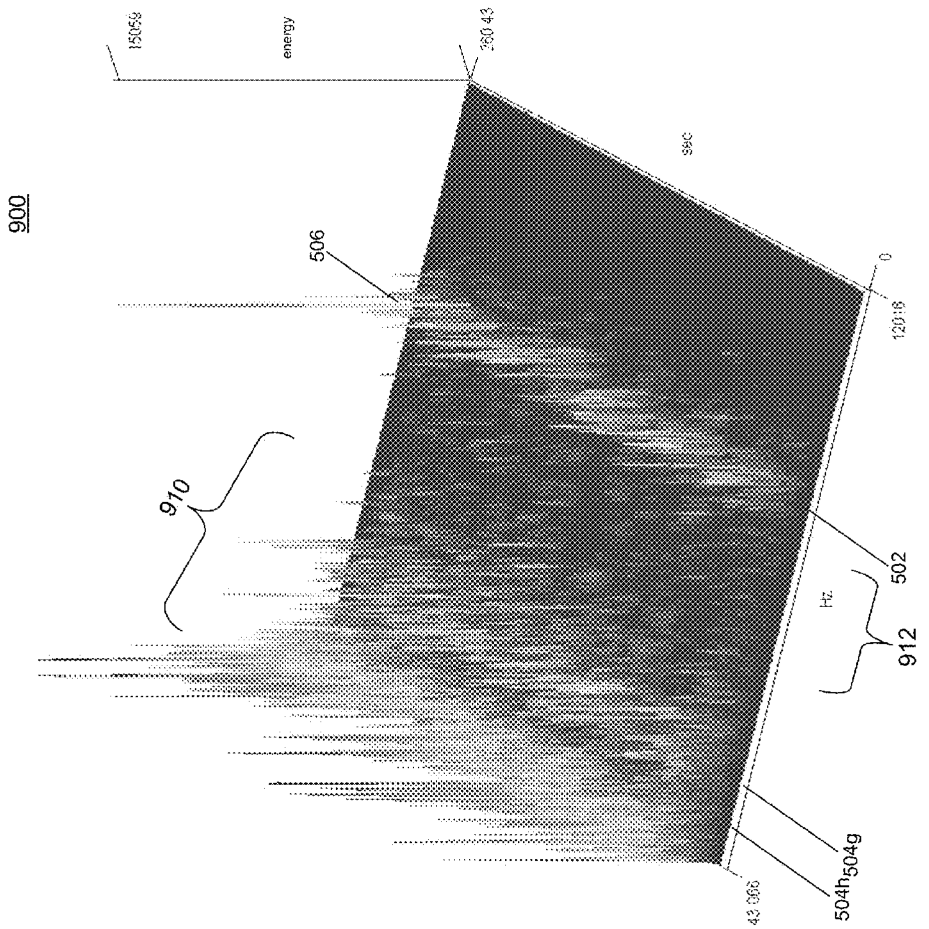
FIG. 9 illustrates an example of a masking sound, in accordance with one aspect of the subject disclosure.

FIG. 8 illustrates another method 800 for treating tinnitus, in accordance with one aspect of the subject disclosure. Method 800 may comprise determining a tinnitus frequency of a patient (802). In some aspects, the tinnitus frequency of a patient may be determined according to the techniques described above. Method 800 also comprises providing a primary audio signal centered about the tinnitus frequency (804). Providing such a primary audio signal is also described above, in accordance with various aspects of the subject disclosure. Method 800 also comprises combining the primary audio signal with a general audio signal to generate a masking sound for treating tinnitus, the general audio signal comprising a sub-octave frequency of the tinnitus frequency (806). For example, FIG. 9 illustrates masking sound 900, which comprises primary audio signal 506 and general audio signal 910, in accordance with one aspect of the subject disclosure. Primary audio signal 506 may be centered about tinnitus frequency 502. Masking sound 900 may be generated similarly as described above with respect to masking sound 500 of FIG. 5. However, general audio signal 910, instead of secondary audio signals 508, may be combined with primary audio signal 506 to generate masking sound 900. While secondary audio signals 508 comprise audio signals centered about octave frequencies 504 of tinnitus frequency 502, general audio signal 910 may comprise a range of frequencies not specifically centered about a certain frequency. Even so, a similar type of masking may be achieved (e.g., as compared to masking sound 500) because general audio signal 910 comprises one or more sub-octave frequencies 504 (e.g., 504*g* and 504*h*) of tinnitus frequency 502.

General audio signal 910 may comprise white noise, a music signal, one or more pure tones, one or more chords, one or more modulated sounds, one or more ambient sounds, a voice signal, or a combination thereof. For example, general audio signal 910 may be music, a book on tape or other sounds. In this way, primary audio signal 506 may be combined with music or other sounds to generate masking sound 900. General audio signal 910, such as music, may comprise frequencies that "fill" the space of sub-octave frequencies 504 to produce the masking effect as described above. However, in some aspects, the high range of musical frequency may be about 4 kHz. Thus, if tinnitus frequency 502 is above this range, there may be a region 912 where the music, or general audio signal 910, does not "fill" the sub-octave frequencies 504 of tinnitus frequency 502 in region 912. According to various aspects of the subject disclosure, secondary audio signals 508 may be combined with general audio signal 910 and primary audio signal 506 to generate masking sound 900. In some aspects, secondary audio signals 508 may be centered about sub-octave frequencies 504 that are in region 912, that is, in frequencies that are beyond the bandwidth of general audio signal 910. Thus, for example, if tinnitus frequency 502 is about 8 kHz, a secondary audio signal 504 may be added at 4 kHz, which may be in a region where general audio signal 910, in the form of music, may not have any signals. On the other hand, if tinnitus frequency 502 is about 5 kHz, the first sub-octave frequency would be 2.5 kHz. In such a case, general audio signal 910, in the form of music, may comprise enough musical content at the first sub-octave frequency such that secondary audio signals 504 may not be needed.

The relative perceived intensity between the intensity of primary audio signal 506 and an intensity of general audio signal 910 may also be adjusted according to the techniques described above. In this case, however, the calibration audio signal may be centered about a frequency within a bandwidth of general audio signal 910. General audio signal 910 may also comprise the calibration audio signal. Thus, the relative perceived intensity between the intensity of primary audio signal 506 and an intensity of general audio signal 910 may be adjusted according to the techniques described above. Furthermore, the left/right balance of primary audio signal 506 and the left/right balance of general audio signal 910 may also be adjusted according to a subjective relative intraaural intensity of the tinnitus, according to the techniques described above. For example, an additional intraaural intensity tuner may be added, with a slider to adjust for the intraaural intensity of general audio signal 910.

Referring to FIGS. 4, 7 and 9, masking sound 900 may also be made available from website 400, according to the techniques described above. For example, website 400 may collect information pertaining to the patient's tinnitus. Website 400 may also provide various audio files for the patient to download as general audio signal 910. Website 400 may generate masking sound 900 by combining primary audio signal 506 with general audio signal 910. Masking sound 900 may be in a way, wmv, mp3, midi, or any other suitable audio format. The patient may then download masking sound 900 from website 400. Masking sound 900 may also be downloadable into an audio device. In this way, the patient may listen to masking sound 900 either on a computer or on any other suitable audio device for playing back audio files. Masking sound 900 may be played with earphones 700, for example, for masking for several hours a day. For example, earphones 700 may be INAIR TECHNOLOGY earphones, which have devices that allow delivery of sound through tragal transmission, allowing the external auditory canal to be open for detection of ambient sounds. This means that masking can occur throughout the day, at work, during driving, and during most daily activities.

According to various aspects of the subject disclosure, a patient may also provide general audio signal 910 to website 400, such that website 400 may generate masking sound 900 by combining primary audio signal 506 and general audio signal 910. For example, a patient may select a general audio signal 910 by using general audio signal selector 428 and activating button 408. General audio signal 910 may be stored on the patient's computer. In some aspects, general audio signal 910 may be uploaded to website 400 so that website 400 may generate masking sound 900 by combining primary audio signal 506 and general audio signal 910. In some aspects, general audio signal 910 is not uploaded to website 400. Rather, website 400 may generate masking sound 900 by providing primary audio signal 506 to the user and then primary audio signal 506 with general audio signal 910, which may still be stored on the patient's computer. In other words, at least part of the processing of the audio signals to generate masking sound 900 may occur on the user's computer. This provides the added advantage of conserving internet bandwidth, as the user may not have to upload general audio signal 910. In an example, a patient may select a song stored on the patient's computer and select that particular song to be general audio signal 910. Thus, website 400 may generate masking sound 900 comprising the song and primary audio signal 506. In some aspects, additional secondary audio signals 508 may be added to masking sound 900.

According to various aspects of the subject disclosure, the energy of general audio signal 910 may be amplified, for example with band-enhance filters, at portions centered about sub-octave frequencies 504 of tinnitus frequency 502 such that the masking effect may be enhanced. For example, website 400 may allow for amplification of a narrow band around tinnitus frequency 502 or octave frequencies 504 for any general audio signal 910 applied to masking sound 900.

In some aspects, the frequency of general audio signal 910 (or a portion of general audio signal 910) may be shifted in order to match tinnitus frequency 502. For example, if tinnitus frequency 502 is about 8 kHz, and general audio signal 910 comprises music, for example, with an upper range of about 2.5 kHz, then general audio signal 910 may be shifted to higher frequencies such that general audio signal 910 may comprise sub-octave frequencies 504 located in region 912. Thus, if general audio signal 910 comprises music, then the music may be shifted and adjusted in terms of frequency and pitch such that the music may comprise octave frequencies of the tinnitus frequency.

Figure 10:
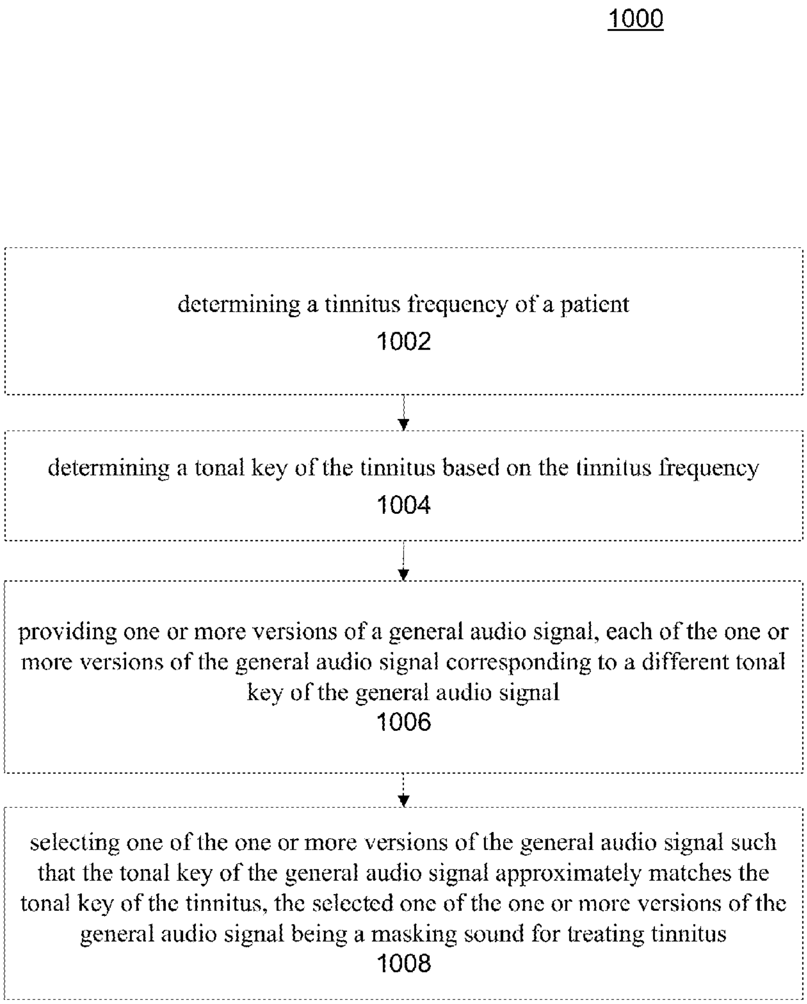
FIG. 10 illustrates a method for treating tinnitus, in accordance with one aspect of the subject disclosure.

FIG. 10 illustrates a method 1000 for treating tinnitus, in accordance with one aspect of the subject disclosure. Method 1000 may comprise determining a tinnitus frequency of a patient (1002). The tinnitus frequency of a patient may be determined according to the techniques described above. Method 1000 also comprises determining a tonal key of the tinnitus (e.g., tinnitus tonal key) based on the tinnitus frequency (1004). The fact that the tinnitus frequency can be characterized may allow for a characterization of the tonal key (e.g., "Key" or chroma) of the tinnitus.

FIG. 11 illustrates an example of determining a tonal key of the tinnitus based on the tinnitus frequency, in accordance with one aspect of the subject disclosure. Referring to FIGS. 10 and 11, after a patient's tinnitus frequency is determined, the tinnitus frequency may be compared to frequency reference range 1102. Frequency reference range 1102 may comprise a number of frequencies that correspond to certain keys 1104 (e.g., chroma). In some aspects, frequency reference range may comprise the octave starting at A3 (220 Hz) and ending at A4 (440 Hz, aka concert pitch). However, other frequency reference ranges are possible. In some aspects, seven or twelve distinct keys may be used. The tinnitus frequency (or an octave frequency of the tinnitus frequency) may then be compared with frequency reference range 1102 to determine which frequency within frequency reference range 1102 is closest to or can approximately match the tinnitus frequency (or an octave frequency of the tinnitus frequency). The key 1104 corresponding to this frequency within frequency reference range 1102 may then be determined to be the tonal key of the tinnitus.

For example, the following chart illustrates various possibilities for the tinnitus frequency, and the resulting tonal key (e.g., tinnitus chroma) that is determined for the tinnitus frequency:

| Tinnitus frequency (Hz) | Frequency within Frequency Reference Range 1102 (Hz) | Octave Distance | Tonal Key of the Tinnitus |
|---|---|---|---|
| 13512 | 422.25 | 5 | G#/Af |
| 8100 | 253.125 | 5 | B3 |
| 4157 | 259.82 | 4 | C4 |
| 127 | 254 | 1 | B3 |

Referring back to FIG. 10, method 1000 also comprises providing one or more versions of a general audio signal, each of the one or more versions of the general audio signal corresponding to a different tonal key of the general audio signal (1006). Method 1000 also comprises selecting one of the one or more versions of the general audio signal ("the selected version") such that the tonal key of the general audio signal approximately matches the tonal key of the tinnitus. The selected version of the general audio signal may be a masking sound for treating tinnitus (1008). The masking sound may be downloadable into an audio device. The masking sound may also be played with earphones, which comprise one or more speakers that sit outside an ear canal of the patient when the earphones are worn by the patient.

By matching the tonal key of the general audio signal with the tonal key of the tinnitus, a masking effect may be produced to treat tinnitus, in accordance with one aspect of the subject disclosure. The selected version of the general audio signal may comprise a music signal, one or more pure tones, one or more chords, one or more modulated sounds, one or more ambient sounds, a voice signal, or a combination thereof. For example, the general audio signal may be a music signal, and thus, musical therapy may be provided to treat tinnitus. A library of music files may be provided such that different versions of each music file may be provided, with each version corresponding to a different tonal key of the music file or a different orchestration of the music file. In some aspects, the music files may be original musical compositions developed specifically for treating tinnitus.

Determining the tonal key of the tinnitus may provide a much more targeted starting point from which to apply musical therapy to tinnitus rehabilitation. Music files may be utilized and selected based on their tonality to conform best to the tonality of the tinnitus frequency. A library of music may be compiled that is written for each of the seven major keys of the Western tonal system. In some aspects, music from this library may be selected based on keys and may then be pitch adjusted up or down to the nearest major key (that approximates the tinnitus frequency), such that the tonal key of the music matches the tonal key of the tinnitus. Contrapunctal compositions may be included in these libraries, as they exploit octave relationships by design. Furthermore, band-enhance filters may be applied that may allow amplification of the octaves that coincide with the tinnitus frequency.

Secondary audio signals as described above (e.g., secondary audio signals 508 of FIG. 5) may also be provided or added to the masking sound, in accordance with various aspects of the subject disclosure. Each of the secondary audio signals may be centered about a sub-octave frequency of the tinnitus frequency. In some aspects, the secondary audio signal may be centered about a sub-octave frequency of the tinnitus frequency beyond the bandwidth of the selected version of the general audio signal.

According to various aspects of the subject disclosure, a relative perceived intensity between an intensity of the tonal key of the tinnitus and an intensity of a calibration audio signal may be adjusted. In some aspects, the calibration audio signal may be centered about a frequency of the selected version of the general audio signal. In some aspects, the selected version of the general audio signal may comprise the calibration audio signal. The relative perceived intensity may be adjusted by providing the calibration audio signal, and a range of intensities of the calibration audio signal. For example, as described above with reference to FIG. 4, a patient may adjust the position of slider 420*b* to adjust the intensity of the calibration audio signal played on website 400. The patient may adjust the intensity of the calibration audio signal such that a perceived intensity of the calibration audio signal, as played on website 400, approximately matches a perceived intensity of the tonal key of the patient's tinnitus. In this way, the intensity of the calibration audio signal, and thus the general audio signal, may be calibrated to approximately the same intensity as the intensity of the tonal key of the patient's tinnitus. In some aspects, additional multiple versions of the selected version of the general audio signal may be provided, where each version of the selected version of the general audio signal corresponds to a different intensity. A version corresponding to a desired intensity may be selected to match a perceived intensity of the tonal key of the patient's tinnitus.

In accordance with various aspects of the subject disclosure, the left/right balance of the selected version of the general audio signal may be adjusted according to a subjective relative intraaural intensity of the tinnitus. This left/right balance of general audio signal may be adjusted according to the techniques described above. In some aspects, additional multiple versions of the selected version of the general audio signal may be provided, where each version of the selected version of the general audio signal corresponds to a different left/right balance. A version corresponding to a desired left/right balance may be selected to according to a subjective relative intraaural intensity of the tinnitus.

According to various aspects of the subject disclosure, general audio signals may be created de novo for treating tinnitus given certain inputs. That is, general audio signals may be created specifically for treating tinnitus. An instrument that has an adjustable timbre may be used, where the timbre is in part defined by the octave distance to the tinnitus frequency. In this way, the general audio signals played by the instrument may at least partially stimulate those auditory neurons that lie on the edge of the region of injury. That is, if those neurons are stimulated, it can induce inhibition to those otherwise hyperactive neurons.

In one example, referring to both FIGS. 10 and 11, suppose general audio signal comprises a music signal, such as a simple song like "Twinkle twinkle little star" (TTLS). For a person with tinnitus at 8100 Hz, TTLS may be played in the key of B with an electronic instrument that has a timbre that reports 5 octaves, with emphasis on the 5th octave. In another example, for a person with tinnitus at 4157 Hz, TTLS may be played in the key of C with an electronic instrument that has a timbre that reports 4 octaves, with emphasis on the 4th octave. In some aspects, the timbre or characteristics of this instrument may be defined by the tinnitus frequency. The tinnitus intensity may help gauge how much energy that may be needed in that region.

According to various aspects of the subject disclosure, pseudo-randomly created musical pieces may be generated. For example, suppose that a tonal key of the tinnitus is C4. The general audio signal matching such a tonal key may then play a3 at pre-defined points, but may then switch in between pre-defined consonant notes, the order of which may be randomly generated. So, in this example, a general audio signal such as a song may comprise the following keys: C4-X-X, where X can be either e4, g4, or c5, and the tempo may be "1-2-3 . . . ." Thus, the general audio signal may sound like: C4-e4-c5-C4-g4-g4-C4-c5-g4 . . . etc.

FIG. 12 illustrates a method 1200 for treating tinnitus, in accordance with one aspect of the subject disclosure. Method 1200 may comprise exposing the patient to an audio signal so that the patient hears the audio signal, to diminish a perception by the patient of tinnitus. The audio signal may comprise (a) a primary peak portion that is substantially centered at about a tinnitus frequency of the patient, and (b) one or more secondary peak portions, each of which is substantially centered at about a respective frequency different from the tinnitus frequency. In some aspects, at least one of: (a) a portion of the audio signal between the primary peak portion and at least one of the secondary peak portions is substantially inaudible; and (b) a portion of the audio signal between any two adjacent secondary peak portions is substantially inaudible (1202).

In some aspects, during an induction phase, patients may listen to a masking sound (e.g., audio signal) as much as possible. For example, the audio signal may be listened to at about 7 to 9 hours a day. In some aspects, the audio signal may be listened to less than about 7 hours a day. In some aspects, the audio signal may be listened to greater than about 9 hours a day. The induction phase may last between about 1 to 3 weeks. In some aspects, the induction phase may last for less than about 1 week. In some aspects, the induction phase may last greater than about 3 weeks. For example, some patients may find that the masking provided by the audio signal to be so effective in reducing the annoyance of tinnitus that they may extend an induction phase use for a longer period of time. In some aspects, the induction phase may be intended to drive tetanic inhibition in the lesion projection zone.

According to various aspects of the subject disclosure, during a maintenance phase, masking may be used for a couple of hours per day or even every other day. In some aspects, masking may be used between more than one day apart. In some aspects, during a maintenance phase, masking may be used only at those times where tinnitus continues to present significance annoyance. Patients may find that their need for maintenance use may continue to decrease and may eventually end altogether. In some aspects, maintenance use may fluctuate. For example, patients may find that maintenance use is increased during times of stress, but is reduced during times of relative calm.

In some aspects, the patient's tinnitus frequency, or an intensity or perception of the tinnitus frequency, may change. Patients may recalibrate the tinnitus frequency. In some aspects, the masking as described herein may be adaptable and dynamic. For example, during an induction phase, patients may recalibrate their masking sounds. In some aspects, the masking sounds may be recalibrated at least every day. In some aspects, the masking sounds may be recalibrated more frequently. Recalibration may ensure that the sound energy may be most appropriately directed towards the hyperactive areas of the brain that most need the treatment. The masking sounds may be recalibrated as often as desired, which may be particularly beneficial to patients with highly variable tinnitus. In some aspects, separate masking sounds may be used for patients with several tones for their tinnitus, and the masking sounds may be switched off as needed. In some aspects, the separate masking sounds may be combined to generate a combined masking sound so that the patient may listen to the combined masking sound at the same time for treating tinnitus. In some aspects, recalibrating may be given its ordinary meaning. In some aspects, recalibrating the tinnitus frequency may refer to repeating the determining of the tinnitus frequency, and/or vice versa.

In some aspects, various metrics for tinnitus severity may be used to track patient progress. For example, some patients may take a "tinnitus annoyance scale" questionnaire, which may, for example, be on website 400. Patients may take this questionnaire during an induction phase, for example, every three days during this phase. In some aspects, patients may take this questionnaire more or less frequently. In some aspects, patients may still take this questionnaire during maintenance to observe patient progress. Graphic displays of patient trends may be available on website 400 or a personalized subset or home page of website 400.

In some aspects, the masking sound may be generated by taking a sample of white noise (e.g., randomly generated signal across all frequencies) and applying a bandpass filter to produce "white noise" within a defined frequency range. In some aspects, this may be the primary peak portion of the audio signal. The bandwidth of this sample may be up to ½ of an octave around the tinnitus frequency. For example, the bandwidth may be ⅓ of an octave around the tinnitus frequency. In some aspects, the masking sound may carry the left/right balance characteristics as determined previously. In some aspects, a bandpass filter, for example at ⅓ of an octave, may be applied at around octave and/or sub-octave frequencies of the tinnitus frequency. In some aspects, this may be the secondary peak portions of the audio signal. In some aspects, separate audio signals may be used, where one audio signal may comprise the primary peak portion and another audio signal may comprise the secondary peak portions. In such a case, the two separate audio signals may be mixed or combined into one audio signal to generate the masking sound.

In some aspects, a sample of the masking sound may be played to the patient. The patient may adjust the intensity or left/right balance of this sample. Once the patient is satisfied, another sample of the masking sound may be taken (e.g., a 2 second sample) and looped so that it may last for a defined length. For example, the sample may be looped to last for one hour. In some aspects, the loop length and/or the sample may be greater or lower. In some aspects, the masking sound may be downloaded to and/or played from an audio device (e.g., mp3 player) for therapeutic use.

Figure 13:
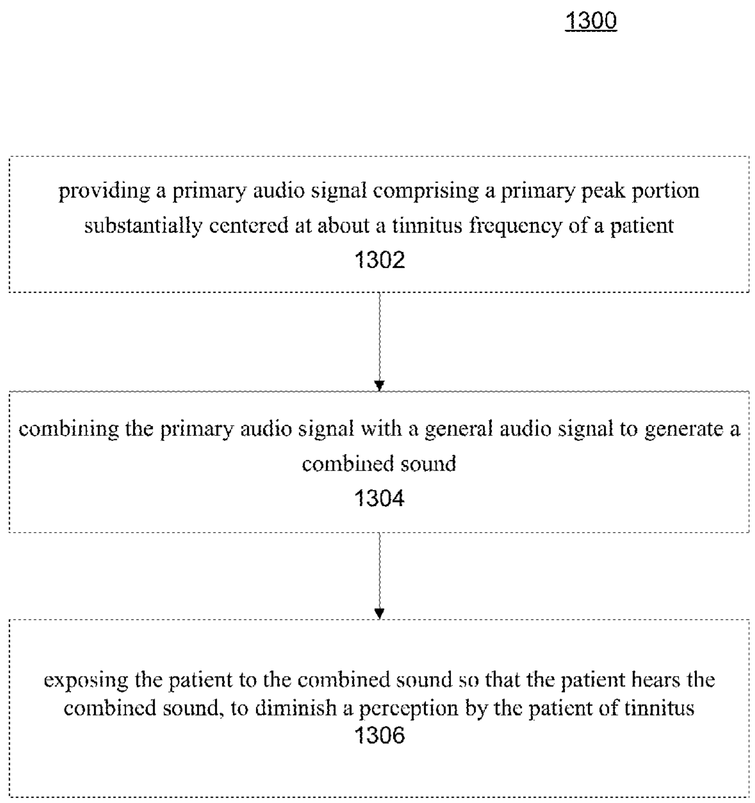
FIG. 13 illustrates a method for treating tinnitus, in accordance with one aspect of the subject disclosure.

FIG. 13 illustrates a method 1300 for treating tinnitus, in accordance with one aspect of the subject disclosure. Method 1300 may comprise providing a primary audio signal comprising a primary peak portion substantially centered at about a tinnitus frequency of a patient (1302). Method 1300 may also comprise combining the primary audio signal with a general audio signal to generate a combined sound (1304). Method 1300 may also comprise exposing the patient to the combined sound so that the patient hears the combined sound, to diminish a perception by the patient of tinnitus (1306).

In some aspects, the general audio signal may comprise a music signal (or any other general audio signal such as spoken word, environmental sounds, etc.). In such a case, method 1300 may be referred to as music therapy. Music may have clear associations with the limbic system, the part of the brain that is responsible for emotion. Even passive listening to pleasant music can positively stimulate structures of the limbic system and elicit pathways associated with pleasant emotive states. As it happens, tinnitus may exert its toxic effects via negative associations developed in the limbic system. Music therapy may utilize the neural circuitry of the limbic system to transform the negative emotive states associated with tinnitus into the positive emotive states associated with music.

In some aspects, the combined sound (e.g., masking sound) may be generated by fusing a patient's preferred music file(s) with targeted masking energy at the patient's tinnitus frequency. Doing so may derail the hyperactivity in the auditory cortex that may drive the tinnitus and create new neural circuits via the limbic system that may be associated with positive emotive states. Music therapy may allow the patient to adjust the intensity of the combined sound according to the intensity of their tinnitus. As the perception of tinnitus diminishes, the user may be able to decrease the presence of the masking sound until it is almost inaudible. In some aspects, patients may utilize music therapy only after the induction phase, which may ensure optimal results. For example, music therapy may be made available two weeks after induction begins. In some aspects, patients may utilize music therapy before or during the induction phase.

In some aspects, a patient may determine the tinnitus frequency by using a slider bar (e.g., slider 412) that may go from low to high frequencies to match the sound from the slider bar with the patient's tinnitus. This process may be repeated to obtain an average, which may be determined to the tinnitus frequency. A test tone (e.g., arbitrarily at 440 hz) may be played to the patient, and then the tinnitus frequency. The patient may then adjust the loudness (e.g., intensity) of the tone at the tinnitus frequency so that it may match that of the test tone. A left/right balance bar (e.g., sliders 424) may be displayed so that the patient can adjust the intensity to match the interaural differences in the tinnitus, if any.

In some aspects, a patient may select a music file (or any other audio file), for example, by uploading it to website 400. In some aspects, this may be the general audio signal. In some aspects, the primary audio signal may be generated by taking a sample of white noise (e.g., randomly generated signal across all frequencies) and applying a bandpass filter to produce "white noise" within a defined frequency range. In some aspects, this may be the primary peak portion of the primary audio signal. The bandwidth of this sample may be up to ½ of an octave around the tinnitus frequency. For example, the bandwidth may be ⅓ of an octave around the tinnitus frequency. In some aspects, the primary audio signal may carry the left/right balance characteristics as determined previously.

In some aspects, the general audio signal and the primary audio signal may be mixed and/or combined to provide the combined sound. The intensity of the general audio signal relative to the intensity of the primary audio signal may also be adjusted according to the techniques described above. A sample of the combined sound may be played to a patient. The patient may adjust the intensity and/or the left/right balance if desired. In some aspects, the patient may adjust the intensity and left/right balance such that the primary audio signal is audible, but not too uncomfortably loud or distracting. Once the patient is satisfied, the combined sound may be downloaded to and/or played from an audio device (e.g., mp3 player) for therapeutic use.

FIG. 14 illustrates a method 1400 for treating tinnitus, in accordance with one aspect of the subject disclosure. Method 1400 may comprise determining a tinnitus tonal key based on a tinnitus frequency of a patient (1402). Method 1400 may also comprise providing a plurality of audio signals, each of the audio signals having a different primary tonal key from each other (1404). In some aspects, a primary tonal key may refer to the tonal key that an audio signal (e.g., a musical song) may be written in. For example, a song may be written in the primary tonal key of "B flat." Method 1400 may also comprise selecting one of the audio signals such that the primary tonal key of the selected audio signal approximately matches the tinnitus tonal key (1406). Method 1400 may also comprise exposing the patient to the selected audio signal so that the patient hears the selected audio signal, to diminish a perception by the patient of tinnitus (1408).

In some aspects, the tinnitus frequency may be determined as described above. The tinnitus tonal key may be derived by determining its logarithmic/and or exponential relationship to tonal keys in the musical range. A plurality of audio signals may be provided. For example, a library of songs may be provided, where songs may be written in different primary tonal keys. Audio signals approximately matching the tinnitus tonal key may be selected. The patient may then choose an audio signal from this selection to listen to for treating tinnitus.

Figure 15:
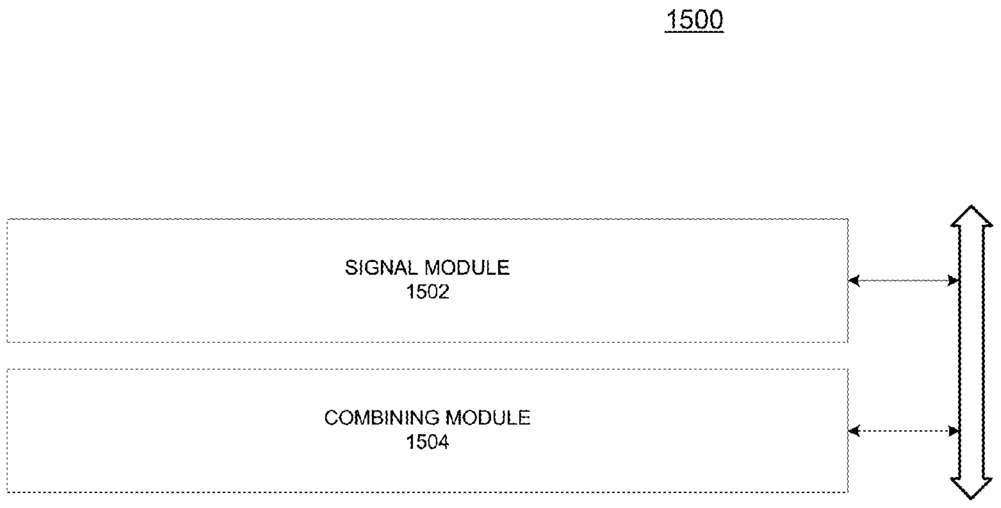
FIG. 15 illustrates an example of a configuration of a system for treating tinnitus, in accordance with one aspect of the subject disclosure.

FIG. 15 illustrates an example of a configuration of a system 1500 for treating tinnitus, in accordance with one aspect of the subject disclosure. System 1500 may comprise a signal module 1502 and a combining module 1504. Signal module 1502 may provide a primary audio signal comprising a primary peak portion substantially centered at about a tinnitus frequency of a patient. Combining module 1504 (*a*) may combine the primary audio signal with a general audio signal to generate a combined signal, and (b) store the combined signal as a file in computer-readable medium. In some aspects, the file, when read in a user listening device that permits the patient to hear the combined signal, diminishes a perception by the patient of tinnitus. In some aspects, at least one of the general audio signal and the primary audio signal may comprise a secondary peak portion substantially centered at about a frequency different from the tinnitus frequency. In some aspects, the secondary peak portion is substantially centered at about an octave or sub-octave frequency of the tinnitus frequency.

Figure 16:
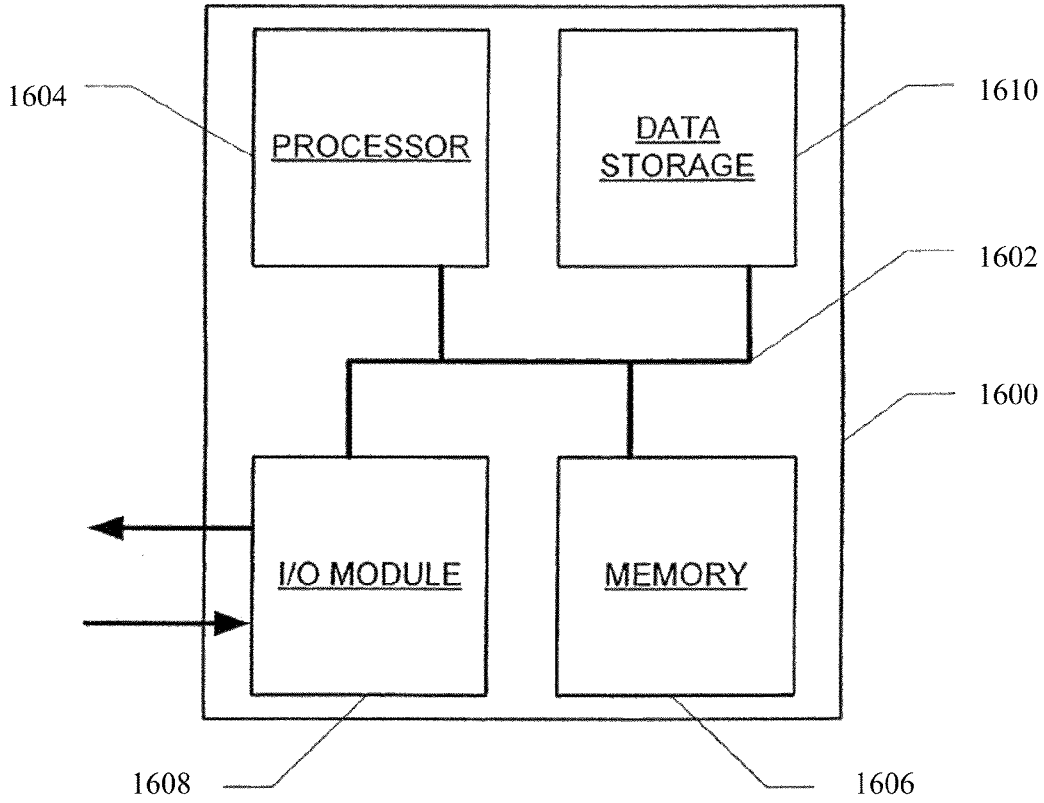
FIG. 16 is a block diagram illustrating an example of a computer system, in accordance with one aspect of the subject technology.

FIG. 16 is a block diagram illustrating an example of a computer system, in accordance with one aspect of the subject technology. In one aspect, computer system 1600 may be utilized to implement an embodiment of the subject technology. Computer system 1600 includes a bus 1602 or other communication mechanism for communicating information, and a processor 1604 coupled with bus 1602 for processing information. Computer system 1600 also includes a memory 1606, such as a random access memory ("RAM") or other dynamic storage device, coupled to bus 1602 for storing information and instructions to be executed by processor 1604. Memory 1606 may also be used for storing temporary variables or other intermediate information during execution of instructions by processor 1604. Computer system 1600 further includes a data storage device 1610, such as a magnetic disk or optical disk, coupled to bus 1602 for storing information and instructions.

Computer system 1600 may be coupled via I/O module 1608 to a display device (not illustrated), such as a cathode ray tube ("CRT") or liquid crystal display ("LCD") for displaying information to a computer user. An input device, such as, for example, a keyboard or a mouse may also be coupled to computer system 1600 via I/O module 1608 for communicating information and command selections to processor 1604.

According to various aspects of the subject disclosure, methods for treating tinnitus may be performed by computer system 1600 in response to processor 1604 executing one or more sequences of one or more instructions contained in memory 1606. Such instructions may be read into memory 1606 from another machine-readable medium, such as data storage device 1610. Execution of the sequences of instructions contained in main memory 1606 causes processor 1604 to perform the process steps described herein. One or more processors in a multi-processing arrangement may also be employed to execute the sequences of instructions contained in memory 1606. In alternative embodiments, hard-wired circuitry may be used in place of or in combination with software instructions to implement various embodiments of the subject technology. Thus, aspects of the subject disclosure are not limited to any specific combination of hardware circuitry and software.

The term "machine-readable medium" as used herein refers to any medium that participates in providing instructions to processor 1604 for execution. Such a medium may take many forms, including, but not limited to, non-volatile media, volatile media, and transmission media. Non-volatile media include, for example, optical or magnetic disks, such as data storage device 1610. Volatile media include dynamic memory, such as memory 1606. Transmission media include coaxial cables, copper wire, and fiber optics, including the wires that comprise bus 1602. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The methods for treating tinnitus described herein may be implemented by various means. For example, these techniques may be implemented in hardware, software, or a combination thereof. For a hardware implementation, the providing, generating, combining, analyzing, shifting, amplifying, or processing of audio signals may be implemented by spectrum analyzers, computers, audio instruments, or other suitable components designed to perform the functions described herein, or a combination thereof. The processing units used in the techniques to treat tinnitus as described herein may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof.

For a software implementation, the techniques used to treat tinnitus as described herein may be implemented with modules (e.g., procedures, functions, and so on) that perform the functions described herein. The software codes may be stored in a memory unit (e.g., memory 1606) and executed by a processor (e.g., processor 1604). The memory unit may be implemented within the processor or external to the processor, in which case it can be communicatively coupled to the processor via various means as is known in the art.

In some aspects, the phrase "substantially" as used herein may be given its ordinary meaning. In some aspects, "substantially" may refer to within 20% of a frequency. In some aspects, "substantially" may refer to within 10% of a frequency. In some aspects, "substantially" may refer to within 5% of a frequency. In some aspects, white noise, as used herein, is to be construed broadly and may refer to pseudo random white noise over a finite frequency spectrum or a component thereof. For example, in some aspects, white noise as used herein may refer to bandwidth limited white noise. In some aspects, all portions between peaks of a signal(s) may be substantially inaudible. In some aspects, the methods and systems described herein may be implemented over a computer network. In some aspects, a computer network may comprise an intranet, an internet, and/or world wide web. In some aspects, harmonic frequencies of the tinnitus frequency (e.g. integer multiples of the tinnitus frequency) may be used instead of or in combination with octave frequencies of the tinnitus frequency as described above. For example, signals and/or peak portions as used herein may be substantially centered at about a supraharmonic or subharmonic frequency of the tinnitus frequency. In some aspects, supraharmonic frequencies may be referred to as harmonic frequencies.

In some aspects, the subject technology as described herein may be applied to treat other conditions in addition to and/or instead of tinnitus. For example, the subject technology may be used to treat hyperacusis and/or acute, subacute and chronic noise-induced hearing loss/acoustic trauma.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

There may be many other ways to implement the invention. Various functions and elements described herein may be partitioned differently from those shown without departing from the sprit and scope of the invention. Various modifications to these configurations will be readily apparent to those skilled in the art, and generic principles defined herein may be applied to other configurations. Thus, many changes and modifications may be made to the invention, by one having ordinary skill in the art, without departing from the spirit and scope of the invention.

Furthermore, to the extent that the term "include," "have," or the like is used in the description or the claims, such term is intended to be inclusive in a manner similar to the term "comprise" as "comprise" is interpreted when employed as a transitional word in a claim.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method for treating tinnitus, comprising:

exposing a patient to an audio signal so that the patient hears the audio signal, to diminish a perception by the patient of tinnitus;

wherein the audio signal comprises (a) a primary peak portion with a bandwidth of a half octave or less substantially centered around a tinnitus frequency of the patient, and (b) one or more secondary peak portions, each of which has a bandwidth of a half octave or less that is substantially centered around a respective frequency different from the tinnitus frequency;

wherein at least one of: (a) a portion of the audio signal between the primary peak portion and at least one of the secondary peak portions is substantially inaudible; and (b) a portion of the audio signal between any two adjacent secondary peak portions is substantially inaudible; and wherein the patient directly hears the primary peak portion and the one or more secondary peak portions simultaneously, wherein the one or more secondary peak portions and the primary peak portion do not overlap.

2. The method of claim 1, wherein each of at least one of the one or more secondary peak portions has a bandwidth of a half octave or less that is substantially centered around a respective octave or sub-octave frequency of the tinnitus frequency.

3. The method of claim 1, further comprising determining the tinnitus frequency of the patient, the determining comprising:

providing to the patient a range of frequencies of one or more test audio signals;

in each of a plurality of trials, receiving from the patient a selection of a frequency, chosen from the range of frequencies, approximately matching the tone of the tinnitus frequency of the patient; and determining an average tinnitus frequency, based on an average of the selected frequencies from the plurality of trials.

4. The method of claim 3, wherein the steps of determining the tinnitus frequency of the patient are conducted by the patient using a website on the Internet.

5. The method of claim 1, further comprising adjusting, based on input from the patient, a bandwidth of at least one of (a) the primary peak portion, and (b) the one or more secondary peak portions.

6. The method of claim 1, wherein the audio signal further comprises at least one of: a component of white noise, a music signal, a pure tone, a chord, a modulated sound, an ambient sound, and a voice signal.

7. The method of claim 1, further comprising adjusting, based on input from the patient, an intensity of the primary peak portion in relation to at least one of the one or more secondary peak portions.

8. The method of claim 1, further comprising adjusting, based on input from the patient, a left/right balance of the primary peak portion and a left/right balance of at least one of the one or more secondary peak portions.

9. The method of claim 1, further comprising: providing earphones to the patient;

wherein the earphones comprise at least one speaker; wherein the earphones, when worn by the patient, do not occlude an ear canal of the patient and allow ambient sound to reach an ear drum of the patient; and wherein the audio signal is transmitted to the at least one speaker.

10. A method for treating tinnitus, comprising:

providing a primary audio signal comprising a primary peak portion with a bandwidth of a half octave or less that is substantially centered around a tinnitus frequency of a patient;

combining the primary audio signal with a general audio signal to generate a combined sound; and exposing the patient to the combined sound so that the patient directly hears the combined sound, to diminish a perception by the patient of tinnitus.

11. The method of claim 10, wherein at least one of the general audio signal and the primary audio signal comprises a secondary peak portion with a bandwidth of a half octave or less that is substantially centered around a frequency different from the tinnitus frequency.

12. The method of claim 11, wherein the secondary peak portion has a bandwidth of a half octave or less that is substantially centered around an octave or a suboctave frequency of the tinnitus frequency.

13. The method of claim 11, wherein the primary audio signal comprises the secondary peak portion;

wherein at least a portion of the primary audio signal between the primary peak portion and the secondary peak portion is substantially inaudible.

14. The method of claim 10, wherein the general audio signal further comprises at least one of: white noise, a music signal, a pure tone, a chord, a modulated sound, an ambient sound, and a voice signal.

15. The method of claim 10, further comprising adjusting, based on input from the patient, an intensity of the primary audio signal in relation to the general audio signal.

16. A computer-implemented system for treating tinnitus, comprising:

a signal module that provides a primary audio signal comprising a primary peak portion with a bandwidth of a half octave or less that is substantially centered around a tinnitus frequency of a patient; and a combining module that (a) combines the primary audio signal with a general audio signal to generate a combined signal, and (b) stores the combined signal as a file in a non-transitory computer-readable medium;

wherein the file, when read in a user listening device that permits the patient to directly hear the combined signal, diminishes a perception by the patient of tinnitus.

17. The system of claim 16, wherein at least one of the general audio signal and the primary audio signal comprises a secondary peak portion with a bandwidth of a half octave or less that is substantially centered around a frequency different from the tinnitus frequency.

18. The system of claim 17, wherein the secondary peak portion has a bandwidth of a half octave or less that is substantially centered around an octave or a suboctave frequency of the tinnitus frequency.

19. The system of claim 17, wherein the primary audio signal comprises the secondary peak portion;

wherein at least a portion of the primary audio signal between the primary peak portion and the secondary peak portion is substantially inaudible.

20. The system of claim 16, wherein the general audio signal further comprises at least one of: white noise, a music signal, a pure tone, a chord, a modulated sound, an ambient sound, and a voice signal.

21. The system of claim 16, configured to perform a method of adjusting, based on input from the patient, an intensity of the primary audio signal in relation to the general audio signal.

* * * * *